US006331523B1

(12) United States Patent
Kljavin et al.

(10) Patent No.: US 6,331,523 B1
(45) Date of Patent: *Dec. 18, 2001

(54) METHOD OF ENHANCING THE SURVIVAL OF RETINAL NEURONS AND TREATING OCULAR DISEASES USING FGF-5

(75) Inventors: Ivar J. Kljavin, Lafayette; Monique La Fleur, Daly City, both of CA (US)

(73) Assignee: Genentech, Inc., South San Francisco, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/240,952

(22) Filed: Jan. 29, 1999

Related U.S. Application Data

(63) Continuation-in-part of application No. 09/041,383, filed on Mar. 12, 1998, now abandoned.

(51) Int. Cl.[7] ........................... A61K 38/16; A61K 38/18

(52) U.S. Cl. ........................... 514/12; 514/56; 514/912; 514/913; 514/914; 435/69.1; 435/69.4; 435/810; 530/350; 530/399; 206/569

(58) Field of Search ..................... 514/12, 56, 912–914; 435/69.1, 69.4, 810; 530/350, 399; 206/569

(56) References Cited

U.S. PATENT DOCUMENTS

| 5,180,820 | 1/1993 | Barde et al. | 530/399 |
|---|---|---|---|
| 5,438,121 | 8/1995 | Barde et al. | 530/399 |
| 5,629,284 | 5/1997 | Unoki | 514/2 |
| 5,693,775 | 12/1997 | Nathans et al. | 530/399 |

FOREIGN PATENT DOCUMENTS

| WO 88/09378 | 12/1988 | (WO) . |
|---|---|---|
| WO 90/12597 | 11/1990 | (WO) . |
| WO 91/03568 | 3/1991 | (WO) . |
| WO 93/08826 | 5/1993 | (WO) . |
| WO 93/25684 | 12/1993 | (WO) . |
| WO 94/01124 | 1/1994 | (WO) . |
| WO 94/20125 | 9/1994 | (WO) . |
| WO 95/20125 | 9/1994 | (WO) . |
| WO 95/15176 | 6/1995 | (WO) . |
| WO 95/24928 | 9/1995 | (WO) . |
| WO 97/30155 * | 8/1997 | (WO) . |
| WO/98/16644 | 4/1998 | (WO) . |

OTHER PUBLICATIONS

*Report of the Retinal and Choroidal Panel: Vision Research—A National Plan 1983–1987* 2(part I):2.

Adler, R., "Mechanisms of Photoreceptor Death in Retinal Degenerations. From the Cell Biology of the 1990s to the Ophthalmology of the 21st Century?" *Archives of Ophthalmology* 114(1):79–83 (Jan. 1996).

Berson et al., "A randomized trial of vitamin A and vitamin E supplementation for retinitis pigmentosa" *Archives of Ophthalmology* 111(6):761–762 (Jun. 1993).

Bird, "Investigation of disease mechanisms in retinitis pigmentosa" *Opthalmic Paediatrics & Genetics* 13(2):57–66 (Jun. 1992).

Bost et al., "Coexpression of the FGF–5 and bFGF by the retinal pigment epithelium in vitro" *Experimental Eye Research* 55(5):727–734 (Nov. 1992).

Caruelle et al., "Immunological study of acidic fibroblast growth factor (aFGF) distribution in the eye" *Journal of Cellular Biochemistry* 39(2):117–128 (Feb, 1989).

Cepko, C., "Immortalization of neural cells via retrovirus–mediated oncogene transduction" *Annual Review of Neuroscience* 12:47–65 (1989).

Clements et al., "Activation of fibroblast growth factor (FGF) receptors by recombinant human FGF–5" *Oncogene* 8:1311–1316 (1993).

Connolly et al., "Localization of bFGF in Developing Retinas of Normal and RCS Rats" *Investigative Ophthalmology & Visual Science* (abstract 440) 32(Supplement):754 (1991).

Cook et al., "Apoptotic Photoreceptor Degradation in Experimental Retinal Detachment" *Investigative Ophthalmology & Visual Science* 36(6):990–996 (May 1995).

Edward et al., "Amelioration of light–induced retinal degradation by a calcium overload blocker. Flunarizine" *Archives of Ophthalmology* 109(4):554–562 (Apr. 1991).

(List continued on next page.)

Primary Examiner—F. Moozie
(74) *Attorney, Agent, or Firm*—David A. Carpenter, PLLC

(57) ABSTRACT

The present invention relates to the use of FGF-5 polypeptides to delay, prevent or rescue retinal neurons, including photoreceptors, other retinal cells or supportive cells (e.g. Müller cells or RPE cells) from injury and degradation. Conditions comprehended by treatment of the present FGF-5 polypeptides (including variants), antibodies, compositions and articles of manufacture include: retinal detachment, age-related and other maculopathies, photic retinopathies, surgery-induced retinopathies (either mechanically or light-induced), toxic retinopathies including those resulting from foreign bodies in the eye, diabetic retinopathies, retinopathy of prematurity, viral retinopathies such as CMV or HIV retinopathy related to AIDS, uveitis, ischemic retinopathies due to venous or arterial occlusion or other vascular disorder, retinopathies due to trauma or penetrating lesions of the eye, peripheral vitreoretinopathy, and inherited retinal degenerations. Exemplary retinal degenerations include e.g., hereditary spastic paraplegia with retinal degeneration (Kjellin and Barnard-Scholz syndromes), retinitis pigmentosa, Stargardt disease, Usher syndrome (refinitis pigmentosa with congenital hearing loss), and Refsum syndrome (retinitis pigmentosa, hereditary hearing loss, and polyneuropathy). Additional disorders which result in death of retinal neurons include, retinal tears, detachment of the retina and pigment epithelium, degenerative myopia, acute retinal necrosis syndrome (ARN), traumatic chorioretinopathies or contusion (Purtscher's Retinopathy) and edema.

18 Claims, 12 Drawing Sheets

OTHER PUBLICATIONS

Faktorovich et al., "Photoreceptor degeneration in inherited retinal dystrophy delayed by basic fibroblast growth factor" *Nature* 347:83–86 (Sep. 6, 1990).

Ferrara et al., "Purification and Cloning of Vascular Endothelial Growth Factor Secreted by Pituitary Folliculostellate Cells" *Methods in Enzymology* 198:391–405 (1991).

Gass, J., "Idiopathic senile macular hole. Its early stages and pathogenesis" *Archives of Ophthalmology* 106(5):629–639 (May 1988).

Gospodarowicz et al., "Isolation of brain fibroblast growth factor by heparin–Sepharose affinity chromatography: identity with pituitary fibroblast growth factor" *Proc. Natl. Acad. Sci. USA* 81(22):6963–6967 (Nov. 1984).

Gouras et al., "Transplanted Photoreceptors Identified in Dystrophic Mouse Retina by a Transgenic Reporter Gene" *Investigative Ophthalmology & Visual Science* 32(13):3167–3174 (Dec. 1991).

Hageman et al., "Sequestration of basic fibroblast growth factor in the primate retinal interphotoreceptor matrix" *Proc. Natl. Acad. Sci. USA* 88(15):6706–6710 (Aug. 1, 1991).

Hammes et al., "Nerve growth factor prevents both neuroretinal programmed cell death and capillary pathology in experimental diabetes" *Molecular Medicine* 1(5):527–534 (Jul. 1995).

Hargrave and O'Brien, "Speculations on the Molecular Basis of Retinal Degradation in Retinitis Pigmentosa" *Retinal Degenerations,* Anderson et al., Boca Raton, FL:CRC Press, Chapter 47, pp. 517–528, (1991).

Haub et al., "Expression of the murine fibroblast growth factor 5 gene in the adult central nervous system" *Proc. Natl. Acad. Sci. USA* 87(20):8022–8026 (Oct. 1990).

Jacquemin et al., "Localization of acidic fibroblast growth factor (aFGF) mRNA in mouse and bovine retina by in situ hybridization" *Neuroscience Letters* 116(1–2):23–28 (Aug. 14, 1990).

Kljavin et al., "Muller cells are a preferred substrate for in vitro neurite extension by rod photoreceptor cells" *Journal of Neuroscience* 11(10):2985–2994 (Oct. 1991).

Lam et al., "Amelioration of retinal photic injury in albano rats by dimethylthiourea" *Archives of Ophthalmology* 108(12):1751–1757 (Dec. 1990).

LaVail et al., "Multiple growth factors, cytokines, and neurothrophins rescue photoreceptors from the damaging effects of constant light" *Proc. Natl. Acad. Sci. USA* 89(23):11249–11253 (Dec. 1, 1992).

Lavail et al., "Retinal pigment epithelial cell transplantation in RCS rats: normal metabolism in rescued photoreceptors" *Experimental Eye Research* 55(4):555–562 (Oct. 1992).

Li and Turner, "Inherited retinal dystrophy in the RCS rat: prevention of photoreceptor degeneration by pigment epithelial cell transplantation" *Experimental Eye Research* 47(6):911–917 (Dec. 1988).

Li et al., "Amelioration of retinal photic injury by a combination of flunarizine and dimethylthiourea" *Experimental Eye Research* 56(1):71–78 (Jan. 1993).

Lindholm et al., "Fibroblast growth factor–5 promotes differentiation of cultured rat septal cholinergic and raphe serotonergic neurons: comparison with the effects of neurotrophins" *European Journal of Neuroscience* 6(2):244–252 (Feb. 1, 1994).

Milam, A., "Strategies for rescue of retinal photoreceptor cells" *Current Opinion in Neurobiology* 3(5):797–804 (Oct. 1993).

Miyake et al., "Structure and expression of a novel member, FGF–16, on the fibroblast growth factor family" *Biochemical & Biophysical Research Communications* 243(1):148–152 (Feb. 4, 1998).

Mullen and LaVail, "Inherited retinal dystrophy: primary defect in pigment epithelium determined with experimental rat chimeras" *Science* 192(4241):799–801 (May 21, 1976).

Organisciak et al., "The protective effect of ascorbate in retinal light damage of rats" *Investigative Ophthalmology & Visual Science* 26(11):1580–1588 (Nov. 1985).

Peyman et al., "A technique for retinal pigment epithelium transplantation for age–related macular degeneration secondary to extensive subfoveal scarring" *Ophthalmic Surgery* 22(2):102–108 (Feb. 1991).

Polverini et al., "Assay and purification of naturally occurring inhibitor of angiogenesis" *Methods in Enzymology* 198:440–450 (1991).

Rappolee and Werb, "Macrophage–derived growth factors" *Current Topics in Microbiology and Immunology* 181:87–140 (1992).

Reh et al., "Growth factors in the treatment of degenerative retinal disorders" *Ciba Foundation Symposium* 196:120–131 (1996).

Reme et al., "Light–Induced Apoptosis in the Rat Retina In Vivo: Morphological Features, Threshold and Time Course" *Degenerative Diseases of the Retina,* Anderson et al., New York:Plenum Press, Chapter 3, pp. 19–25 (1995).

Rosner et al., "Methylprednisolone ameliorates retinal photic injury in rats" *Archives of Ophthalmology* 110(6):857–861 (Jun. 1992).

Sheedlo et al., "Photoreceptor Rescue in the Dystrophic Retina by Transplantation of Retinal Pigment Epithelium" *International Review of Cytology* 138:1–49 (1992).

Silverman and Hughes, "Photoreceptor rescue in the RCS rat without pigment epithelium transplantation" *Current Eye Research* 9(2):183–191 (Feb. 1990).

Thomas, K., "Purification and characterization of acidic fibroblast growth factor" *Methods in Enzymology* 147:120–135 (1987).

Wong, F., "Photoreceptor apoptosis in animal models. Implications for retinitis pigmentosa research" *Archives of Ophthalmology* 113(10):1245–1247 (Oct. 1995).

Zhan et al., "The human FGF–5 oncogene encodes a novel protein related to fibroblast growth factors" *Molecular & Cellular Biology* 8(8):3487–3495 (Aug. 1988).

* cited by examiner

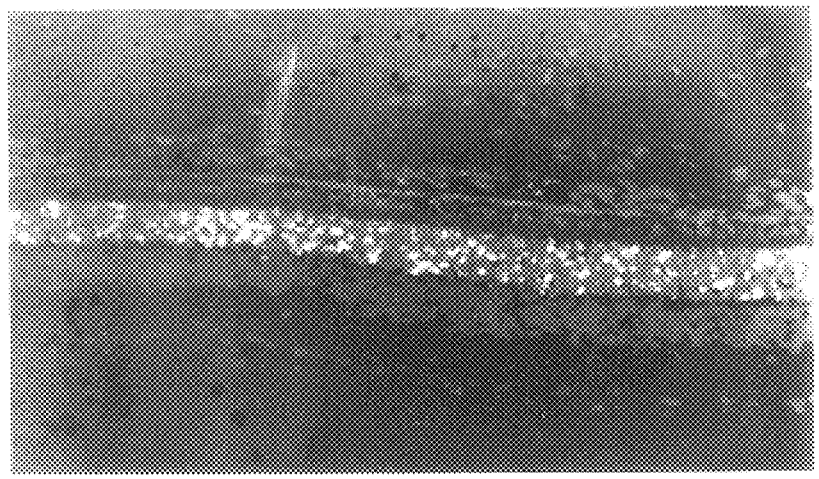
FIG. 3A  Saline
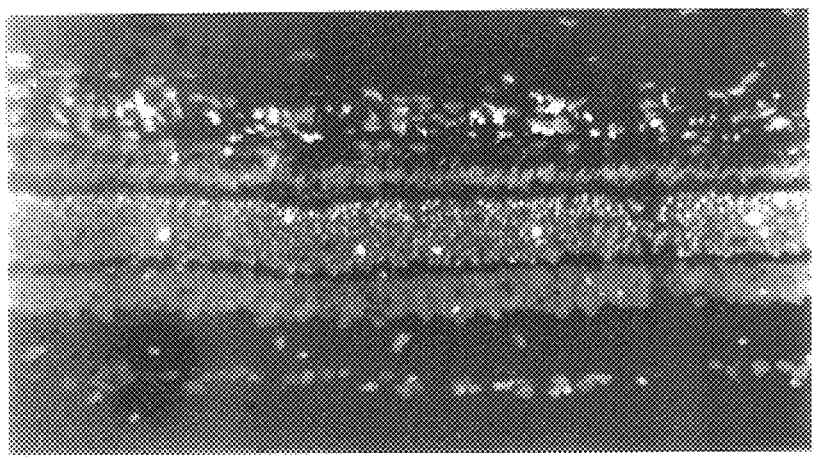
FIG. 3B  bFGF
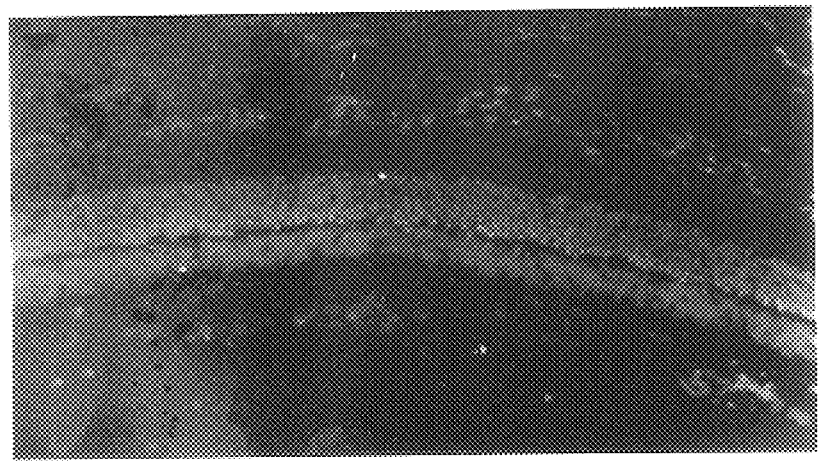
FIG. 3C  FGF-5

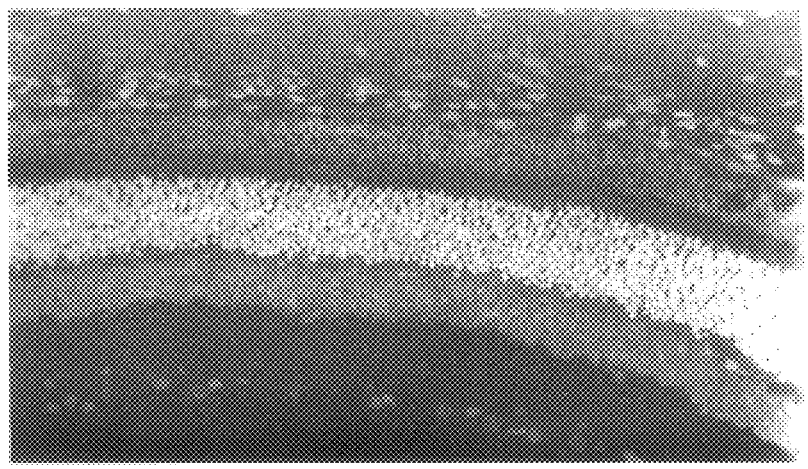
FIG. 4A    No light
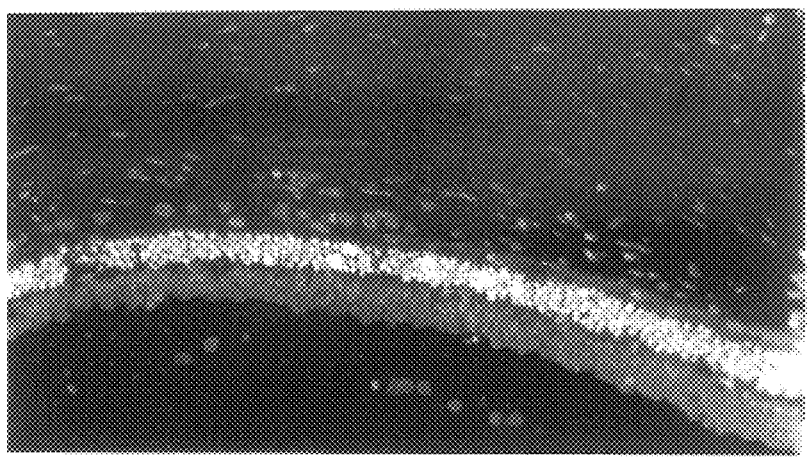
FIG. 4B    50 hrs post cycle
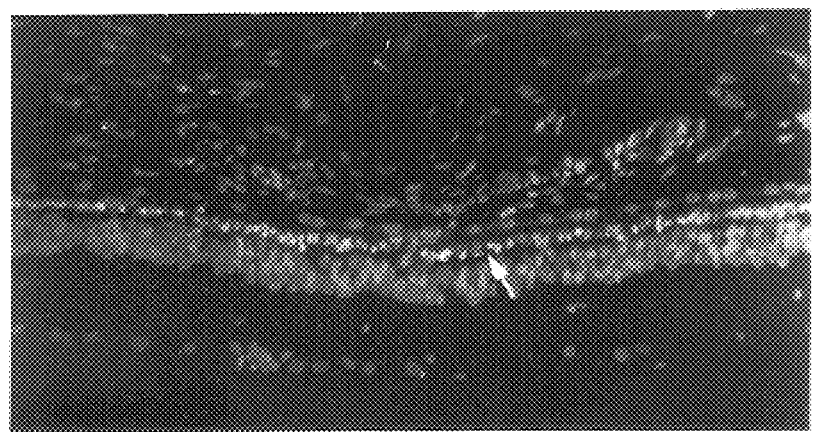
FIG. 4C    7 days post cycle

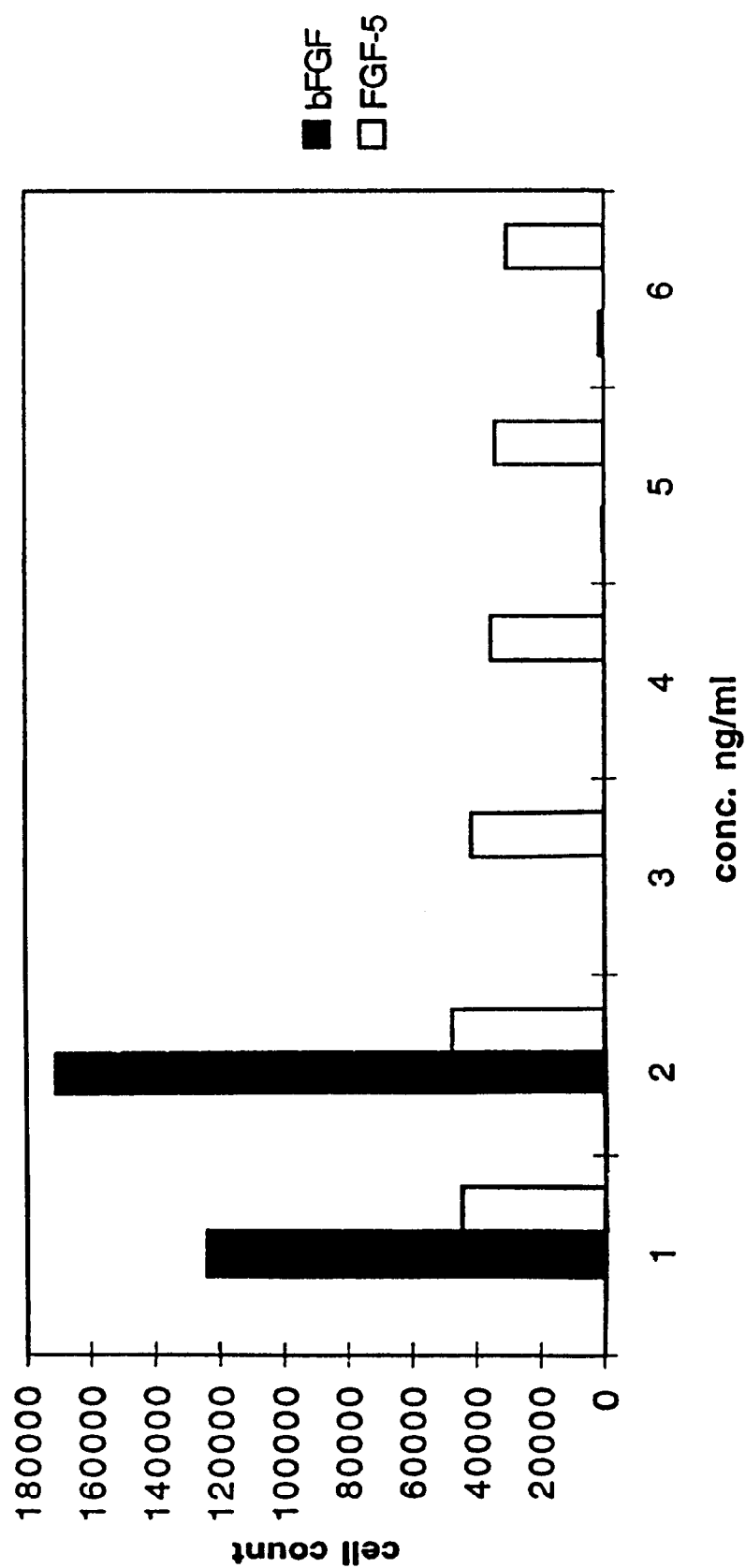

(SEQ ID NO: 1)
(SEQ ID NO: 3)

```
  1 TCTAGAAAAT AAGGAGGAAA AAAAAATGGG TGAAAAACGT CTGGCTCCGA AAGGTCAGCC TGGTCCGGCT GCCACTGATA GGAACCCTAG AGGCTCCAGC
    AGATCTTTTA TTCCTCCTTT TTTTTTACCC ACTTTTTGCA GACCGAGGCT TTCCAGTCGG ACCAGGCCGA CGGTGACTAT CCTTGGGATC TCCGAGTCG
  1                      M  G  E  K  R  L  A  P  K  G  Q  P  G  P  A  A  T  D  R  N  P  R  G  S  S

101 AGCAGACAGA GCAGCAGTAG CGCTATGTCT TCCTCTTCTG CCTCCCTCTC CCCCGCAGCT TCTCTGGGCA GCCAAGGAAG TGGCTTGGAG CAGAGAGAGTT
    TCGTCTGTCT CGTCGTCATC GCGATACAGA AGGAGAAGAC GGAGGGAGAG AGAGACCCGT CGGTTCCTTC ACCGAACCTC GTCGTCAA
 26  S  R  Q  S  S  S  A  M  S  S  S  A  S  L  G  S  Q  G  S  G  L  E  Q  S  S  F

201 TCCAGTGGAG CCCCTCGGGG CGCCGGACCG GCAGCCTCTA CTGCAGAGTG GGCATCGGTT TCCATCTGCA GATCTACCCG GATGCAAAAG TCAATGATC
    AGGTCACCTC GGGGAGCCCC GCGGCCTGGC CGTCGGAGAT GACGTCTCAC CCGTAGCCAA AGGTAGACGT CTAGATGGGC CTACCGTTTC AGTTACCTAG
 60  Q  W  S  P  S  G  R  R  T  G  S  L  Y  C  R  V  G  I  G  F  H  L  Q  I  Y  P  D  G  K  V  N  G  S

301 CCACGAAGCC AATATGTTAA GTGTTTTGAA AATATTTGCT GTGTCTCAGG GGATTGTAGG AATACGAGGA GTTTTCAGCA ACAAATTTT AGCGATGTCA
    GGTGCTTCGG TTATACAATT CACAAAACCT TTATAAAGCA CACAGAGTCC CCTAACATCC TTATGCTCCT CAAAAGTCGT TGTTAAAA TCGCTACAGT
 93  H  E  A  N  M  L  S  V  L  E  I  F  A  V  S  Q  G  I  V  G  I  R  G  V  F  S  N  K  F  L  A  M  S

401 AAAAAAGGAA AACTCCATGC AAGTGCCAAG TTCACAGATG ACTGCAAGTT CAGGGAGCGT TTTCAAGAAA TACCTATAA TCAGCAATAC
    TTTTTTCCTT TTGAGGTACG TTCACGGTTC AAGTGTCTAC TGACGTTCAA GTCCCTCGCA AAAGTTCTTT TATCGATATT AGTCGTTATG
126  K  K  G  K  L  H  A  S  A  K  F  T  D  D  C  K  F  R  E  R  F  Q  E  N  S  Y  N  T  Y  A  S  A  I  H

501 ATAGAACTGA AAAAACAGGG CGGGAGTGGT ATGTGGCCCT GAATAAAAGA GAACTTTCTT CCTTTTCGT AACGAGGGTG CAGCCCCCGG GTTAAACCCC AGCATATCTC
    TATCTTGACT TTTTTGTCCC GCCCTCACCA TACACCGGGA CTTATTTTCT CTTGAAAGAA GGAAAAGCA TTGCTCCCAC GTCGGGGGCC CAATTTGGG TCGTATAGAG
160  R  T  E  K  T  G  R  E  W  Y  V  A  L  N  K  R  G  K  A  K  R  G  C  S  P  R  V  K  P  Q  H  I  S

601 TACCCATTT CTGCCAAGAT TCAAGCAGTC GGAGCAGCCA GAACTTTCTT TGTTCCTGAA AAGAAAAATC CACCTAGCCC TATCAAGTCA
    ATGGGTAAAA GACGGTTCTA AGTTCGTCAG CCTCGTCGGT CTTGAAAGAA ACAAGGACTT TTCTTTTTAG GTGGATCGGG ATAGTTCAGT
193  T  H  F  L  P  R  F  K  Q  S  E  Q  P  E  L  S  F  T  V  T  V  P  E  K  K  N  P  P  S  P  I  K  S

701 AAGATTCCCC TTTCTGCACC TCGGAAAAAT ACCAACTCAG TGAAATACAG ACTCAAGTTT CGCTTTGAT AAAAAGCTTT ATGAAATCTA ACAATGCGCT
    TTCTAAGGGG AAAGACGTGG AGCCTTTTTA TGGTTGAGTC ACTTATGTC TGAGTTGCAA GCGAAACCTA TTTTTCGAAA TACTTTAGAT TGTTACGCGA
226  K  I  P  L  S  A  P  R  K  N  T  N  S  V  K  Y  R  L  K  F  R  F  G  Q
```

FIG. 8

CONTROL

Human RPE

FGF-5 270 ng/ml

CONTROL

Human RPE

FGF-5 270 ng/ml

CONTROL

Human RPE

FGF-5 270 ng/ml

```
SEQ ID NO:2   fgf5.simmons    1  MSLSFLLLLFFSHLILSAWAHGEKRLAPKGQPGPAATDRNPRGSSSRQSS
SEQ ID NO:3   fgf5.haub       1  ---------------MGEKRLAPKGQPGPAATDRNPRGSSSRQSS
SEQ ID NO:4   fgf5.rd         1  ----------------MEKRLAPKGQPGPAATDRNPRGSSSRQSS fgf5.simmons   51  SSAMSSSSASSSPAASLGSQQGSGLEQSSFQWSPSGRRTGSLYCRVGIGFH
              fgf5.haub      31  SSAMSSSSASSSPAASLGSQQGSGLEQSSFQWSPSGRRTGSLYCRVGIGFH
              fgf5.rd        30  SSAMSSSSASSSPAASLGSQQGSGLEQSSFQWSPSGRRTGSLYCRVGIGFH fgf5.simmons  101  LQIYPDGKVNGSHEANMLSVLEIFAVSQGIVGIRGVFSNKFLAMSKKGKL
              fgf5.haub      81  LQIYPDGKVNGSHEANMLSVLEIFAVSQGIVGIRGVFSNKFLAMSKKGKL
              fgf5.rd        80  LQIYPDGKVNGSHEANMLSVLEIFAVSQGIVGIRGVFSNKFLAMSKKGKL fgf5.simmons  151  HASAKFTDDCKFRERFQENSYNTYASAIHRTEKTGREWYVALNKRGKAKR
              fgf5.haub     131  HASAKFTDDCKFRERFQENSYNTYASAIHRTEKTGREWYVALNKRGKAKR
              fgf5.rd       130  HASAKFTDDCKFRERFQENSYNTYASAIHRTEKTGREWYVALNKRGKAKR fgf5.simmons  201  GCSPRVKPQHISTHFLPRFKQSEQPELSFTVTVPEKKNPPSPIKSKIPLS
              fgf5.haub     181  GCSPRVKPQHISTHFLPRFKQSEQPELSFTVTVPEKKNPPSPIKSKIPLS
              fgf5.rd       180  GCSPRVKPQHISTHFLPRFKQSEQPELSFTVTVPEKKNPPSPIKSKIPLS fgf5.simmons  251  APRKNTNSVKYRLKFRFG
              fgf5.haub     231  APRKNTNSVKYRLKFRFG
              fgf5.rd       230  APRKNTNSVKYRLKFRFG
```

FIG. 10

```
                         SEQUENCE LISTING (1) GENERAL INFORMATION:

(iii) NUMBER OF SEQUENCES: 5

(2) INFORMATION FOR SEQ ID NO: 1:

(i) SEQUENCE CHARACTERISTICS:
            (A) LENGTH: 800 base pairs
            (B) TYPE: Nucleic Acid
            (C) STRANDEDNESS: Single
            (D) TOPOLOGY: Linear (xi) SEQUENCE DESCRIPTION: SEQ ID NO: 1:

TCTAGAAAAT AAGGAGGAAA AAAAAATGGG TGAAAAACGT CTGGCTCCGA             50

AAGGTCAGCC TGGTCCGGCT GCCACTGATA GGAACCCTAG AGGCTCCAGC            100

AGCAGACAGA GCAGCAGTAG CGCTATGTCT TCCTCTTCTG CCTCCTCCTC            150

CCCCGCAGCT TCTCTGGGCA GCCAAGGAAG TGGCTTGGAG CAGAGCAGTT            200

TCCAGTGGAG CCCCTCGGGG CGCCGGACCG GCAGCCTCTA CTGCAGAGTG            250

GGCATCGGTT TCCATCTGCA GATCTACCCG GATGGCAAAG TCAATGGATC            300

CCACGAAGCC AATATGTTAA GTGTTTTGGA AATATTTGCT GTGTCTCAGG            350

GGATTGTAGG AATACGAGGA GTTTTCAGCA ACAAATTTTT AGCGATGTCA            400

AAAAAAGGAA AACTCCATGC AAGTGCCAAG TTCACAGATG ACTGCAAGTT            450

CAGGGAGCGT TTTCAAGAAA ATAGCTATAA TACCTATGCC TCAGCAATAC            500

ATAGAACTGA AAAAACAGGG CGGGAGTGGT ATGTGGCCCT GAATAAAAGA            550

GGAAAAGCCA AACGAGGGTG CAGCCCCCGG GTTAAACCCC AGCATATCTC            600

TACCCATTTT CTGCCAAGAT TCAAGCAGTC GGAGCAGCCA GAACTTTCTT            650

TCACGGTTAC TGTTCCTGAA AAGAAAAATC CACCTAGCCC TATCAAGTCA            700

AAGATTCCCC TTTCTGCACC TCGGAAAAAT ACCAACTCAG TGAAATACAG            750

ACTCAAGTTT CGCTTTGGAT AAAAAGCTTT ATGAAATCTA ACAATGCGCT            800

(2) INFORMATION FOR SEQ ID NO: 2:

(i) SEQUENCE CHARACTERISTICS:
            (A) LENGTH: 268 amino acids
```

(B) TYPE: Amino Acid
        (D) TOPOLOGY: Linear (xi) SEQUENCE DESCRIPTION: SEQ ID NO: 2:

Met Ser Leu Ser Phe Leu Leu Leu Leu Phe Ser His Leu Ile
 1               5                  10                  15

Leu Ser Ala Trp Ala His Gly Glu Lys Arg Leu Ala Pro Lys Gly
                20                  25                  30

Gln Pro Gly Pro Ala Ala Thr Asp Arg Asn Pro Arg Gly Ser Ser
                35                  40                  45

Ser Arg Gln Ser Ser Ser Ser Ala Met Ser Ser Ser Ser Ala Ser
                50                  55                  60

Ser Ser Pro Ala Ala Ser Leu Gly Ser Gln Gly Ser Gly Leu Glu
                65                  70                  75

Gln Ser Ser Phe Gln Trp Ser Pro Ser Gly Arg Arg Thr Gly Ser
                80                  85                  90

Leu Tyr Cys Arg Val Gly Ile Gly Phe His Leu Gln Ile Tyr Pro
                95                  100                 105

Asp Gly Lys Val Asn Gly Ser His Glu Ala Asn Met Leu Ser Val
                110                 115                 120

Leu Glu Ile Phe Ala Val Ser Gln Gly Ile Val Gly Ile Arg Gly
                125                 130                 135

Val Phe Ser Asn Lys Phe Leu Ala Met Ser Lys Lys Gly Lys Leu
                140                 145                 150

His Ala Ser Ala Lys Phe Thr Asp Asp Cys Lys Phe Arg Glu Arg
                155                 160                 165

Phe Gln Glu Asn Ser Tyr Asn Thr Tyr Ala Ser Ala Ile His Arg
                170                 175                 180

Thr Glu Lys Thr Gly Arg Glu Trp Tyr Val Ala Leu Asn Lys Arg
                185                 190                 195

Gly Lys Ala Lys Arg Gly Cys Ser Pro Arg Val Lys Pro Gln His
                200                 205                 210

Ile Ser Thr His Phe Leu Pro Arg Phe Lys Gln Ser Glu Gln Pro
                215                 220                 225

Glu Leu Ser Phe Thr Val Thr Val Pro Glu Lys Lys Asn Pro Pro
                230                 235                 240

Ser Pro Ile Lys Ser Lys Ile Pro Leu Ser Ala Pro Arg Lys Asn
                245                 250                 255

Thr Asn Ser Val Lys Tyr Arg Leu Lys Phe Arg Phe Gly
                260                 265             268

(2) INFORMATION FOR SEQ ID NO: 3:

(i) SEQUENCE CHARACTERISTICS:
        (A) LENGTH: 248 amino acids
        (B) TYPE: Amino Acid
        (D) TOPOLOGY: Linear (xi) SEQUENCE DESCRIPTION: SEQ ID NO: 3:

Met Gly Glu Lys Arg Leu Ala Pro Lys Gly Gln Pro Gly Pro Ala
 1               5                  10                  15

Ala Thr Asp Arg Asn Pro Arg Gly Ser Ser Ser Arg Gln Ser Ser
                20                  25                  30

Ser Ser Ala Met Ser Ser Ser Ser Ala Ser Ser Ser Pro Ala Ala
                35                  40                  45

Ser Leu Gly Ser Gln Gly Ser Gly Leu Glu Gln Ser Ser Phe Gln

```
                            50                  55                  60
Trp Ser Pro Ser Gly Arg Arg Thr Gly Ser Leu Tyr Cys Arg Val
                    65                  70                  75
Gly Ile Gly Phe His Leu Gln Ile Tyr Pro Asp Gly Lys Val Asn
                    80                  85                  90
Gly Ser His Glu Ala Asn Met Leu Ser Val Leu Glu Ile Phe Ala
                    95                 100                 105
Val Ser Gln Gly Ile Val Gly Ile Arg Gly Val Phe Ser Asn Lys
                   110                 115                 120
Phe Leu Ala Met Ser Lys Lys Gly Lys Leu His Ala Ser Ala Lys
                   125                 130                 135
Phe Thr Asp Asp Cys Lys Phe Arg Glu Arg Phe Gln Glu Asn Ser
                   140                 145                 150
Tyr Asn Thr Tyr Ala Ser Ala Ile His Arg Thr Glu Lys Thr Gly
                   155                 160                 165
Arg Glu Trp Tyr Val Ala Leu Asn Lys Arg Gly Lys Ala Lys Arg
                   170                 175                 180
Gly Cys Ser Pro Arg Val Lys Pro Gln His Ile Ser Thr His Phe
                   185                 190                 195
Leu Pro Arg Phe Lys Gln Ser Glu Gln Pro Glu Leu Ser Phe Thr
                   200                 205                 210
Val Thr Val Pro Glu Lys Lys Asn Pro Pro Ser Pro Ile Lys Ser
                   215                 220                 225
Lys Ile Pro Leu Ser Ala Pro Arg Lys Asn Thr Asn Ser Val Lys
                   230                 235                 240
Tyr Arg Leu Lys Phe Arg Phe Gly
                   245         248

(2) INFORMATION FOR SEQ ID NO: 4:

(i) SEQUENCE CHARACTERISTICS:
        (A) LENGTH: 155 amino acids
        (B) TYPE: Amino Acid
        (D) TOPOLOGY: Linear (xi) SEQUENCE DESCRIPTION: SEQ ID NO: 4:

Met Ala Glu Gly Glu Ile Thr Thr Leu Pro Ala Leu Pro Glu Asp
  1                  5                  10                  15
Gly Gly Ser Gly Ala Phe Pro Pro Gly His Phe Lys Asp Pro Lys
                    20                  25                  30
Arg Leu Tyr Cys Lys Asn Gly Gly Phe Phe Leu Arg Ile His Pro
                    35                  40                  45
Asp Gly Arg Val Asp Gly Val Arg Glu Lys Ser Asp Pro His Ile
                    50                  55                  60
Lys Leu Gln Leu Gln Ala Glu Glu Arg Gly Val Val Ser Ile Lys
                    65                  70                  75
Gly Val Cys Ala Asn Arg Tyr Leu Ala Met Lys Glu Asp Gly Arg
                    80                  85                  90
Leu Leu Ala Ser Lys Cys Val Thr Asp Glu Cys Phe Phe Phe Glu
                    95                 100                 105
Arg Leu Glu Ser Asn Asn Tyr Asn Thr Tyr Arg Ser Arg Lys Tyr
                   110                 115                 120
Thr Ser Trp Tyr Val Ala Leu Lys Arg Thr Gly Gln Tyr Lys Leu
                   125                 130                 135
Gly Ser Lys Thr Gly Pro Gly Gln Lys Ala Ile Leu Phe Leu Pro
```

```
                        140              145              150
Met Ser Ala Lys Ser
                155
```

(2) INFORMATION FOR SEQ ID NO: 5:

(i) SEQUENCE CHARACTERISTICS:
        (A) LENGTH: 247 amino acids
        (B) TYPE: amino acid
        (D) TOPOLOGY: Linear (xi) SEQUENCE DESCRIPTION: SEQ ID NO: 5:

```
Met Glu Lys Arg Leu Ala Pro Lys Gly Gln Pro Gly Pro Ala Ala
 1               5                  10                  15

Thr Asp Arg Asn Pro Arg Gly Ser Ser Arg Gln Ser Ser Ser
                20                  25                  30

Ser Ala Met Ser Ser Ser Ala Ser Ser Pro Ala Ala Ser
                35                  40                  45

Leu Gly Ser Gln Gly Ser Gly Leu Glu Gln Ser Ser Phe Gln Trp
                50                  55                  60

Ser Pro Ser Gly Arg Arg Thr Gly Ser Leu Tyr Cys Arg Val Gly
                65                  70                  75

Ile Gly Phe His Leu Gln Ile Tyr Pro Asp Gly Lys Val Asn Gly
                80                  85                  90

Ser His Glu Ala Asn Met Leu Ser Val Leu Glu Ile Phe Ala Val
                95                 100                 105

Ser Gln Gly Ile Val Gly Ile Arg Gly Val Phe Ser Asn Lys Phe
               110                 115                 120

Leu Ala Met Ser Lys Lys Gly Lys Leu His Ala Ser Ala Lys Phe
               125                 130                 135

Thr Asp Asp Cys Lys Phe Arg Glu Arg Phe Gln Glu Asn Ser Tyr
               140                 145                 150

Asn Thr Tyr Ala Ser Ala Ile His Arg Thr Glu Lys Thr Gly Arg
               155                 160                 165

Glu Trp Tyr Val Ala Leu Asn Lys Arg Gly Lys Ala Lys Arg Gly
               170                 175                 180

Cys Ser Pro Arg Val Lys Pro Gln His Ile Ser Thr His Phe Leu
               185                 190                 195

Pro Arg Phe Lys Gln Ser Glu Gln Pro Glu Leu Ser Phe Thr Val
               200                 205                 210

Thr Val Pro Glu Lys Lys Asn Pro Pro Ser Pro Ile Lys Ser Lys
               215                 220                 225

Ile Pro Leu Ser Ala Pro Arg Lys Asn Thr Asn Ser Val Lys Tyr
               230                 235                 240

Arg Leu Lys Phe Arg Phe Gly
               245     247
```

METHOD OF ENHANCING THE SURVIVAL OF RETINAL NEURONS AND TREATING OCULAR DISEASES USING FGF-5

This is a continuation-in-part of application Ser. No. 09/041,383 filed on Mar. 12, 1998 now abandoned, which application is incorporated herein by reference and to which application priority is claimed under 35 USC §120.

BACKGROUND

The present invention relates to a method of promoting retinal neuron survival as well as preventing photoneuron degredation.

The retina is the light-sensitive portion of the eye. The retina contains the cones and rods (photoreceptors), the photosensitive cells. The rods contain rhodopsin, the rod photopigment, and the cones contain 3 distinct photopigments, which respond to light and transmit signals through successive neurons to ultimately trigger a neural discharge in the output cells of the retina, the ganglion cells. The signal is carried by the optic nerve to the visual cortex where it is registered as a visual stimulus.

In the center of the retina is the macula lutea, which is about ⅓ to ½ cm in diarneter. The macula provides detailed vision, particularly in the center (the fovea), because the cones are higher in density. Blood vessels, ganglion cells, inner nuclear layer and cells, and the plexiform layers are all displaced to one side (rather than resting above the ones), thereby allowing light a more direct path to the cones.

Under the retina is the choroid, a collection of blood vessels embedded within a fibrous tissue, and the pigmented epithelium (PE), which overlays the choroid layer. The choroidal blood vessels provide nutrition to the retina (particularly its visual cells). The choroid and PE are found at the posterior of the eye.

The retinal pigment epithelial (RPE) cells, which make up the PE, produce, store and transport a variety of factors that are responsible for the normal function and survival of photoreceptors. RPE are multifunctional cells that transport metabolites to the photoreceptors from their blood supply, the chorio capillaris of the eye. The RPE cells also function to recycle vitamin A as it moves between the photoreceptors and the RPE during light and dark adaptation. RPE cells also function as macrophages, phagocytizing the rhythmically-shed tips of the outer segments of rods and cones, which are produced in the normal course of cell physiology. Various ions, proteins and water move between the RPE cells and the interphotoreceptor space, and these molecules ultimately effect the metabolism and viability of the photoreceptors.

The Müller cell is the most prominent glial cell within the retina, and could also be important for maintaining the viability of visual cells. Müller cells traverse the entire retina in a radial direction from the ganglion cells to the external limiting membrane, a photoreceptor-photoreceptor and Müller cell-photoreceptor contact point. In addition to providing structural support, Müller cells regulate the control of ionic concentrations, degradation of neurotransmitter, removal of certain metabolites and may be a source of important factors that promote the normal differentiation of photoreceptor cells. Kljavin and Reh (1991), *J. Neuroscience* 11: 2985–2994. Although a search for defects in Müller cells has not specifically been examined, any disease or injury affecting their normal function most likely would have a dramatic influence on the health of rods and cones. Finally, the death of rod photoreceptors may influence the viability of cones. One common feature in degenerations involving mutations in rod specific genes (i.e., rhodopsin) is that cones also eventually die. The reason for the loss of cones has not been determined, although it has been suggested that dying rods may release endotoxins. Bird (1992), *Opthal. Pediatric. Genet.* 13: 57–66.

Diseases or injury to the retina can lead to blindness if retinal cells are injured or killed. The photoreceptor cells are particularly susceptible to injury since they are often the first cells to degenerate or suffer damage as a result of a traumatizing event or condition. Hereditary defects in specific photoreceptor genes, retinal detachment, circulatory disorders, overexposure to light, toxic effects to drugs and nutritional deficiencies are among the wide array of causes that can result in the death of photoreceptor cells. Developmental and hereditary diseases of the retina account for around 20 percent of all legal blindness in the United States. *Report of the Retinal and Choroidal Panel: Vision Research—A National Plan* 1983–1987, vol. 2, part I, summary page 2. For example, retinitis pigmentosa (RP), a genetic based progressive disease is characterized by incremental loss of peripheral vision and night blindness, which is due in large part to the loss of photoreceptor cells. RP is a group of hereditary diseases and presently afflicts about one in 3000 persons worldwide. Wong, F. (1995) *Arch. Ophthalmol.* 113: 1245–47. Total blindness is the usual outcome in more progressive stages of this disease. Macular degeneration, another major cause of blindness, is a complex group of disorders that affects the central or predominantly cone portion of the retina. Cones are primarily responsible for acute vision. Diabetic retinopathy, a frequent complication in individuals with diabetes mellitus, is estimated to be the fifth leading cause of new blindness. However, it is the second leading cause of blindness among individuals of 45–74 years of age. Moreover, these problems are only expected to get worse as the general population ages.

Photoreceptor degeneration may also occur as a result of overexposure to light, various environmental trauma or by any pathological condition characterized by death or injury of retinal neurons or photoreceptors.

Photoreceptor loss may also be influenced by cellular or extracellular retinal components. The primary example of extracellular stimulus is related to the close association between the pigment epithelium (PE) and the photoreceptor cells. As mentioned previously, the PE transports metabolites to and from the photoreceptors as well as removes discarded cellular material. Retinal detachment, which involves the separation of the neural retina from the PE leads to photoreceptor death. Furthermore, the degree of cell loss is dependent upon the duration of the separation. Gouras et al. (1991) *IOVS* 32: 3167–3174.

Additionally, diseases of the PE can lead to photoreceptor cell loss. The primary example of this is the Royal College of Surgeons (RCS) rat, which has an inherited retinal dystrophy due to a defect in the PE, resulting in photoreceptor cell death during the normal course of the animal's life. Mullen & LaVail (1976), *Science* 192: 799–801. In this animal, the PE are unable to phagocytize outersegment debris which accumulates between the photoreceptor cells and the PE, and as a result, provide a useful model system to study the role of trophic factors on the retina. A delay of photoreceptor death is obtained through the proximal placement of normal PE cells both in experimental chimeras, Mullen & LaVail, supra and by transplantation of PE from healthy animals. Li & Turner (1988), *Exp. Eye Res.* 47: 911–917; Sheedlo et al. (1992), *Int. Rev. Cytol.* 138: 1–49; Lavail et al. (1992), *Exp. Eye Res.* 55: 555–562; Lavail et al.

(1992), *PNAS* 89: 11249–11253. In all of these experiments, the "rescue" extended beyond the boundaries of the normal PE cells, and suggests the presence of difussible trophic factor(s) produced by the PE cells.

Another useful animal model is the albino rat. In this animal, normal illumination levels of light, if continuous, can cause complete degeneration of photoreceptors. Results obtained using such rats as a model to identify survival enhancing factors appear to correlate well with data obtained using RCS rats. Moreover, different factors can be compared and complications can be assessed more quickly in the light damage model than can be assessed by testing factors in models which are based on the slowly evolving dystrophy of the RCS rat.

Using albino rats, it has been determined that a number of agents, when administered systemically (intraperitoneally) can be used to ameliorate retinal cell death or injury caused by exposure to light. In general, exposure to light generates oxygen free radicals and lipid peroxidation products. Accordingly, compounds that act as antioxidants or as scavengers of oxygen free radicals reduce photoreceptor degeneration. Agents such as ascorbate, Organisciak et al. (1985), *Invest. Opthal. & Vis. Sci.* 26: 1580–1588, flunarizine, Edward et al. (1991), *Arch. Ophthalmol.* 109: 554–562, and dimethylthiourea, Lam et al. (1990), *Arch. Opthal.* 108:1751–1757 have been used to ameliorate the damaging effects of constant light. There is no evidence, however, that these compounds will act to ameliorate other forms of photoreceptor degeneration and their administration can potentiate harmful side effects. Further, these studies are limited because they utilize systemic delivery, which does not provide an adequate means of assessing the effectiveness of a particular factor. As a result, it is nearly impossible to assess the amount of agent that actually reaches the retina. A large amount of agent must be injected to attain a sufficient concentration at the site of the retina. In addition, systemic toxic effects may result from the injection of certain agents.

Traditional approaches to treating the loss of vision due to photoreceptor cell death has taken at least two routes: (1) replacing the defective cells by physical transplantation; and (2) slowing, arresting or preventing the process of degeneration. The transplantation of healthy pigment epithelium cells into a degenerating retina or one which has defective epithelium cells can rescue photoreceptor cells from dying. Sheedlo et al. (1992), *Int. Rev. Cytol.* 138: 1–49); Lavail et al. (1992), *Exp. Eye Res.* 55: 555–562; and Lavail et al. (1992), *PNAS* 89: 11249–11253. PE transplants in humans have been attempted, but the results have been less than satisfactory. Peyman et al. (1991), *Opthal. Surg.* 22: 102–108. More promising, but as yet unproven is the transfer of embryonic retina containing mostly undifferentiated progenitor cells, which can differentiate in response to environmental cues into appropriate missing cell types. Cepko (1989), *Ann. Rev. Neurosci.* 12: 47–65. In conclusion, therapy via functional integration of transplanted retinal cells into a human host retinas remain unproven.

Other strategies have focused on "rescuing" or slowing the loss of visual cells. These techniques include corrective gene therapy, limiting the exposure to normal light during disease, vitamin A supplemented diets and the administration of growth factors to damaged or degenerating eyes. However, these treatment schemes have several limitations.

For example, gene therapy or the insertion of a replacement allele into the cells carrying the known mutation may prove problematic. Milam, *Curr. Opin. Neurobiology* 3: 797–804 (1993). Since rods and cones are somewhat inaccessible, it might be difficult to deliver replacement genes to them. Moreover, the use of retroviral vectors for insertion of replacement genes is limited to dividing cells, such as cultured PE, whereas post-mitotic neurons, e.g. photoreceptors, will require other viral vectors such as HSV (Herpes simplex virus) for effective delivery. Finally, gene replacement may not correct a disease where the mutant gene product is deleterious to the cell, but may be more useful for correcting defects due to the loss-of-function of a gene product, as is found in most recessive disorders.

Limiting light exposure, a low technology conventional approach to attenuating vision loss, typically using such approaches as eye-patches, dark goggles, etc. is impractical, since the practical effect of the treatment is the same as the disease itself: blindness and inability to detect light.

Vitamin A has been observed to halt the decline of retinal function by over 20% as administered over the course of 4–6 years in the progression of patients with retinitis pigmentosa (RP). E. L. Berson et al., *Arch Ophthalmol.* 111: 761–772 (1993). While this study did indicate a potential lengthening of years of useful vision, several criticisms of vitamin A therapy exist: (1) the mechanism by which vitamin A (and even vitamin E) alter the progression of RP is unknown; (2) it is not known whether or not patients with different genetic forms of RP will respond to vitamin A therapy; (3) it is not apparent whether or not quantifiable measurements of visual function (i.e., perimetry and visual acuity) revealed any significant benefit from vitamin A therapy; and (4) long term ingestion of vitamin A may have detrimental side effects in other organ systems.

A number of agents, when administered systemically (intraperitoneally) can be used to ameliorate retinal cell death or injury caused by exposure to light. In general, exposure to light generates oxygen free radicals and lipid peroxidation products. It has been suggested that genetically defective photoreceptors are abnormally sensitive to photooxidation from light levels as encountered normally in the environment. Hargrave, P A. & O'Brien, P J., *Retinal Degenerations*, Anderson R E et al. eds., Boca Raton, Fla., CRC Press, p. 517–528 (1991). Compounds that act as antioxidants or as scavengers of oxygen free radicals reduce photoreceptor degeneration. Anti-oxidants or calcium overload blockers (e.g. flunarizine) have been reported to prevent degeneration of normal photoreceptors after exposure to high light levels. Rosner et al., *Arch. Ophthalmol* 110: 857–861 (1992); Li et al. *Exp. Eye Res.* 56: 71–78 (1993). Additional success in reducing photoreceptor degeneration has been observed through administration of ascorbate (Organisciak et al., *Invest. Ophthal. & Vis. Sci.* 26: 1580–1588 (1985)), flunarizine (Edward et al., *Arch. Ophthalmol.* 109: 554–562 (1991)), and dimethylthiourea (Lam et al., *Arch. Ophthal.* 108: 1751–1757 (1990)). However, there is no evidence that administration of these compounds will reduce photoreceptor degeneration induced by other than intense light exposure. Moreover, there is great concern that their administration can generate potentially harmful side effects. As a result, the search continues for factors which can somehow protect photoreceptors or even promote their regeneration after light-induced damage.

A particular area of interest is the administration of growth factors. Growth factors have been found to participate in diverse roles such as neuronal differentiation, transmitter specificity, regulation of programmed cell death, and neurite growth in several regions of the central nervous system. However, only recently has their role been studied during retinal development and disease. An early study indicating that diffusible growth factors can rescue photoreceptor cells from dying was based on a chimeric rat constructed to contain both normal and RCS pigment epithelial cells. The animals were produced by fusing blastula from both normal and RCS rat embryos. Mullen and LaVail, supra. In the retina of these chimeras, photoreceptor cells adjacent to RCS PE showed degeneration, and those that were lying next to normal PE were healthy. However, photoreceptor cells that were lying just beyond the immediate contact site of normal PE also appeared healthy, suggesting that photoreceptor-PE contact was not needed, and that normal PE were secreting a putative survival promoting factor.

Among the best characterized growth factors in the retina are the acidic and basic fibroblast growth factors (aFGF and bFGF). FGF can be detected through immunohistochemical, biochemical or molecular approaches on a variety of retinal cells including PE, photoreceptor cells and the interphotoreceptor cell matrix (IPM), and a collection of extracellular matrix molecules surrounding photoreceptor cells. Jacquemin et al. (1990) *Neurosci. Lett.* 116: 23–28; Caruelle et al. (1989) *J. Cell Biol.* 39: 117–128; Hageman et al. (1991) *PNAS* 88: 6706–6710; Connolly et al. (1991) *IOVS* 32 (suppl.): 754Intravitreal injection of basic fibroblast growth factor (bFGF) in the RCS rat or rats with light damaged retina prevents photoreceptor cell degeneration for several month, even as outersegment debris accumulates. Faktorovich et al. (1990), *Nature* 347: 83–86. Similar results have been seen when bFGF is injected into the subretinal space, the area between the photoreceptors and the PE. However, even sham operations, or injections of phosphate buffered saline (PBS) in both the RCS rat and light damaged retina can delay photoreceptor cell death. However, the rescue effect is small and localized to the needle track, and differs quantitatively from the effect obtained with bFGF. Faktrorovich et al., supra; Silverman and Hughes (1990), *Curr. Eye Res.* 9: 183–191; Sheedlo H. J. et al., *Int. Rev. Cyto.* 138: 1–49 (1992). In these experiments it is likely that various growth factors derived from damaged retinal tissues or macrophages present in the damaged area were locally released. Sheedlo et al., supra.; Silverman and Hughes, supra. Macrophages themselves are known to produce many different growth factors or cytokines, some of which could have photoreceptor survival activity. Rappolee and Werb, *Curr. Top. Microbiol. Immunol.* 181: 87–140 (1992).

Various agents disclosed to have survival-enhancing and/or growth activity on retinal neurons are described in certain issued patents and pending patent applications. These include Transforming Growth Factor-β (TGF-β) (WO 94/01124), brain derived neurotrophic factors (BDNF) (U.S. Pat. No. 5,180,820) (U.S. Pat. No. 5,438,121) and (WO 91/03568), neurotrophin-4 (NT-4) (WO 93/25684), and insulin-like growth factors (IGF) (WO 93108826).

Other experiments have shown that intravitreal injections of human subretinal fluid as well as other growth factors can rescue dying photoreceptor cells. For example, one recent study tested eight different factors injected into the retina of rats exposed to constant high intensity light, all showing the ability to delay the degeneration of photoreceptor cells. These include FGF (both acidic and basic forms), brain derived neurotrophic factor (BDNF), ciliary neurotrophic factor (CNTF), and interleukin 1 (IL-1). Neurotrophin 3 (NT 3), insulin-like growth factor II (IGF-II), Transforming Growth Factor beta (TGF-β) and the tumor necrosis factors alpha and beta (TNF-α, TNF-β) also showed survival activity, but to a much lesser degree than the other factors. NGF has been reported to reduce the incidence of apoptosis in diabetic rats in addition to minimizing pericyte loss and acellular occluded capillaries, conditions associated with diabetic retinopathy. Hammes, H P et al., *Molecular Med.* 1(5): 527–534 (1995). However, while it does appear that growth factors can enhance survival of photoreceptors, some of these factors may promote detrimental side effects. For example, injections of bFGF results in an increased incidence of macrophages and cataracts. In addition, bFGF is mitogenic for PE, Müller cells and retinal vascular cells. Faktorovich et al., supra.; La Vail et al., supra. As a result, suitable growth factors which will not only promote the survival of photoreceptor cells, but lack undesired side effects have yet to be discovered.

FGF-5 is a member of the fibroblast growth factors (FGF's) which are family of potent mitogens for both normal diploid fibroblasts and established cell lines, Gospodarowicz, D. et al. (1984) *Proc. Nat'l. Acad. Sci. USA* 81:6963FGF-5 was originally identified as a transforming gene by the NIH-3T3 focus formation assay using DNA derived from human tumors. This protein was originally identified as a 267 amino acid residue polypeptide with a putative 22 amino acid residue signal peptide. The FGF family comprises acidic FGF, basic FGF, INT-2 (FGF-3), K-FGF/HST (FGF-4), FGF-5, FGF-6, KGF (FGF-7), AIGF (FGF-8), FGF-9, FGF-10, etc. Recently, a new member of this family, designated FGF-16 has been isolated (Miyake et al., *Biochem. Biophys. Res. Commun.* 243(1): 148–152 (1998). FGFs typically have two conserved cysteine residues and share 30–50% sequence homology at the amino acid level. These factors are mitogenic for a wide variety of normal diploid mesoderm-derived and neural crest-derived cells, including granulosa cells, adrenal cortical cells, chondrocytes, myoblasts, corneal and vascular endothelial cells (bovine or human), vascular smooth muscle cells, and lens epithelial cells. The mitogenicity of FGF-5 is particularly described by 3H-thymidine incorporation in quiescent NR6R-3T3 fibroblasts in Thomas, K., *Methods in Enzymology* 147: 120–135 (1987).

FGF-5 was first disclosed as the gene product of an oncogene called ORF-2, Goldfarb, M. et al., WO 88/09378; Zhan X., et al. (1987) *Oncogene* 1: 369–376; Zhan et al. (1988) *Mol. Cell. Biol.* 8: 3487–3495The protein was originally called FGF-3, owing to its similarity to the previous known a-FGF and b-FGF. However, by the time that the sequence of this molecule had been made publicly available, two additional FGF-related polypeptides, two additional FGF-related polypeptides, INT-2 and HST/K-FGF, had already been described, Zhan et al., 1988, supra. As a result, FGF-3 was redesignated FGF-5. Subsequently, it was found that the sequence described in Zhan et al. is incorrect, and the correct sequence appears in Haub et al., *Proc. Natl. Acad. Sci. USA* 87: 8022–8026 (1990).

FGF-5 has been described to promote the survival and growth of motor neuron cells, and was proposed for the treatment of diseases characterized by the dysfunction of motor neurons (WO 94/20125). FGF-5 was also shown to have activity in the promotion, survival and differentiation of cholinergic septal and serotonergic neurons (WO 95/15176; Lindholm et al., *Eur. J. Neurosci.* 6: 244–252 (1994)). Recombinant FGF-5 (R&D systems) is also known to be mitogenic in Balb/3T3 fibroblasts and bovine heart endothelial cells. R & D Systems data sheet, FGF-5, Cat. No. 237-F5/CF. FGF-5 has also been found to be expressed in the PE, Bost et al., *Exp. Eye Res.* 55: 727–734 (1992), as well as ganglion cells and photoreceptors, Reh et al., *Ciba Found. Symp.* 196: 120–131 (1996).

However, FGF-5 has not been previously known as a potential survival promoting agent for photoreceptor cells.

This is likely due to at least two reasons: (1) Various other known FGFs are mitogenic for retinal cells, especially basic FGF; (2) FGF-5 is mitogenic in fibroblast, endothelial and motor neuronal cells. As a result, its homology to other retinal mitogenic agents as well as the mitogenic character upon non-retinal cells would lead one of ordinary skill in the art to expect FGF-5 to be mitogenic to retinal cells as well.

Surprisingly, Applicants have discovered that FGF-5 prevents the death of photoreceptor cells without any significant mitogenic effect upon photoreceptor cells. Thus, it appears to be an ideally suited candidate for a photoreceptor and/or retinal neuron survival agent.

SUMMARY

The present invention relates to a method of delaying, preventing or rescuing photoreceptor cells from injury or death by the administration of a therapeutically effective amount of an FGF-5 polypeptide.

In another aspect, the present invention relates to the use of FGF-5 polypeptides to delay, prevent or rescue other retinal cells or supportive cells (e.g. Müller cells or RPE cells) from injury and death. Other retinal neurons include, but are not limited to retinal ganglion cells, displaced retinal ganglion cells, amacrine cells, displaced amacrine cells, horizontal and bipolar neurons. Additionally, the invention relates to the use of FGF-5 to stimulate the regeneration of such cells. In one aspect, the FGF-5 polypeptide is an active FGF-5 polypeptide which is at least 90% homologous to a native sequence FGF-5 molecule. In yet another aspect, the FGF-5 polypeptide is an active FGF-5 polypeptide encoded by a nucleotide sequence which hybridizes under stringent conditions to nucleic acid residues 26–769 of SEQ ID NO: 1. In a preferred embodiment, the FGF-5 polypeptide is selected from the group consisting of SEQ ID NO:2, SEQ ID NO: 3 and SEQ ID NO: 5.

In yet another aspect, the present invention relates to the use of FGF-5 polypeptides to treat any condition which results in injury or death of photoreceptor or other retinal cells. Examples of conditions include: retinal detachment; age-related and other maculopathies; photic retinopathies, surgery-induced retinopathies (either mechanically or light-induced), toxic retinopathies including those resulting from foreign bodies in the eye; diabetic retinopathies; retinopathy of prematurity; viral retinopathies such as CMV or HIV retinopathy related to AIDS; uveitis; ischemic retinopathies due to venous or arterial occlusion or other vascular disorder; retinopathies due to trauma or penetrating lesions of the eye; peripheral vitreoretinopathy; and inherited retinal degenerations. Exemplary retinal degenerations include e.g., hereditary spastic paraplegia with retinal degeneration (Kjellin and Barnard-Scholz syndromes), retinitis pigmentosa, Stargardt disease, Usher syndrome (retinitis pigmentosa with congenital hearing loss), and Refsum syndrome (retinitis pigmentosa, hereditary hearing loss, and polyneuropathy). Additional disorders which result in death of retinal neurons include, retinal tears, detachment of the retina and pigment epithelium, degenerative myopia, acute retinal necrosis syndrome (ARN), traumatic chorioretinopathies or contusion (Purtscher's Retinopathy) and edema.

In yet another aspect, the present invention relates to a method of delaying, preventing or rescuing retinal neurons (e.g., photoreceptors) or other retinal cells from injury or death resulting from disease or injury comprising the administration of a composition of FGF-5 polypeptide and a pharmaceutically-acceptable carrier.

In still yet another aspect, the present invention provides articles of manufacture and kits that include FGF-5 polypeptide. The articles of manufacture and kits include a container, a label on the container, and a composition contained within the container. The label on the container indicates that the composition can be used to delay, prevent or rescue retinal neurons or other retinal cells from injury or death. The composition contains an active agent, and the active agent comprises FGF-5.

Other aspects of the invention will become apparent from the following detailed description and the claims.

BRIEF DESCRIPTION OF THE DRAWINGS

FIG. 4 is a negative image photograph representing the normal photoreceptor degredation which occurs open exposure to intense light at 50 hours and 7 days after the cycle described in Example 5.

FIG. 6A is a bar graph comparing the angiogenic effect of bFGF (SEQ ID NO:4) in comparison with FGF-5 (SEQ ID NO:5) at a concentration of 1 ng/ml, 5 ng/ml, 30 ng/ml (FGF-5 only), 100 ng/ml (FGF-5 only), 300 ng/ml (FGF-5 only) and 1000 ng/ml (FGF-5).

FIG. 8 shows a hFGF-5 nucleic acid sequence (SEQ ID NO:1) corresponding to native human FGF-5 minus the native signal sequence (amino acid residues 1–21 of SEQ ID NO:2) and the predicted mature protein sequence (SEQ ID NO:3). The depicted nucleotide sequence (SEQ ID NO:1) (including 5' and 3' vector sequence) is 800 bp in length.

FIG. 9 is a micrograph showing the survival effect in culture of retinal pigmented epithelian cell (RPE) conditioned media and FGF-5 (R&D Sys., lot #40) (SEQ ID NO:5). A indicates immunofluorescent staining of rod photoreceptor cells using a rhodopsin-specific monoclonal antibody, B shows labeling of live cells using cell tracker, and C shows the corresponding phase image.

FIG. 10 shows a comparison between native FGF-5 (fgf-5.simmons), SEQ ID NO:2 as described in Haub et al., *Proc. Natl. Acad. Sci. USA* 87: 8022–8026 (1990) in comparison with the signal peptide-less *E. coli* expression product (fgf-5 haub), SEQ ID NO:3.

DETAILED DESCRIPTION OF THE INVENTION

I. Definitions

Figure 1:
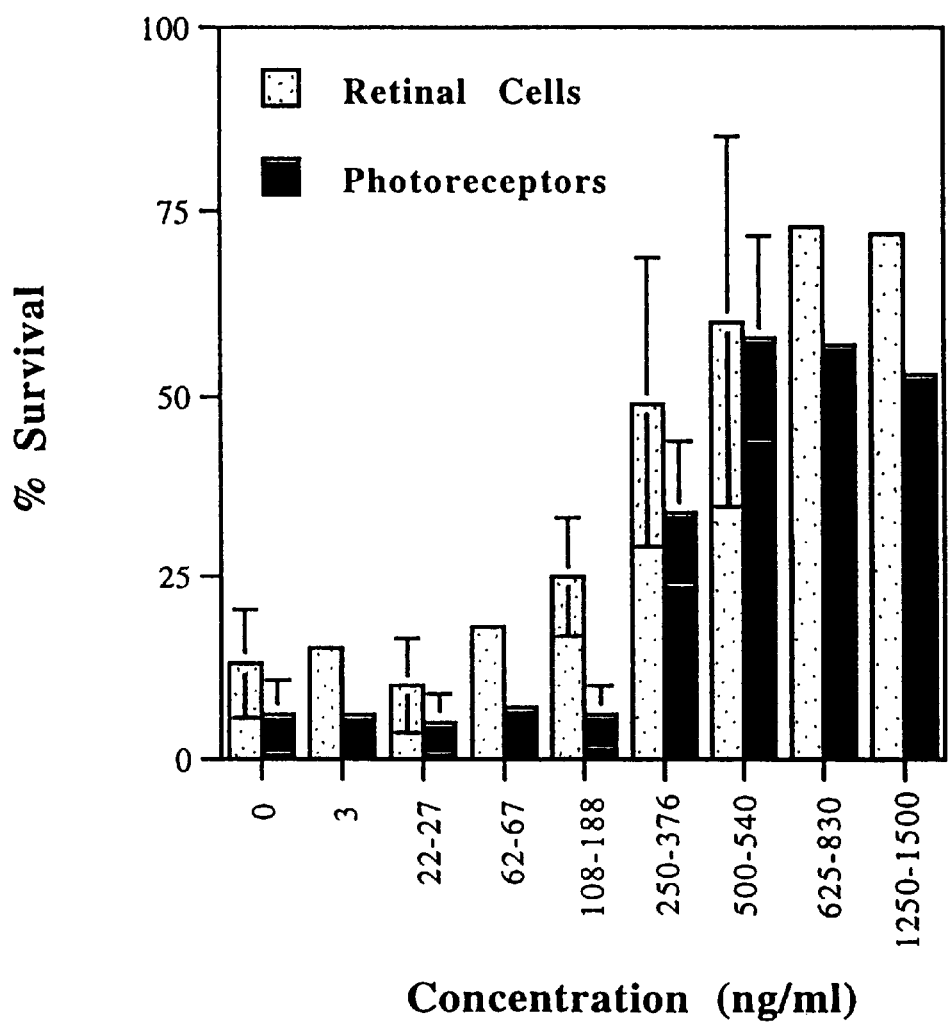
FIG. 1 is a bar graph representing total retinal cell survival and photoreceptor survival in the presence of various concentrations of FGF-5 (SEQ ID NO:5) as administered by the procedure described in Examples 6 and 7, respectively.

The terms employed throughout this application are to be construed with the normal meaning to those of ordinary skill in the art. However, applicants desire that the following terms be construed with the particular definitions as described. All references mentioned in this application should be interpreted and read as being incorporated by reference.

The terms "protein" or "polypeptide" are intended to be used interchangeably. They refer to a chain of two (2) or more amino acids which are linked together with peptide or amide bonds, regardless of post-translational modification (e.g., glycosylation or phosphorylation). The polypeptides of this invention may comprise more than one subunit, where each subunit is encoded by a separate DNA sequence.

The term "FGF-5 polypeptide" is used here to encompass native-sequence FGF-5 protein and variants (which are hereafter defined) which are members of the family of fibroblast growth factors. The FGF-5 polypeptide may be isolated from a variety of sources, such as from human tissue types or from another source, or prepared by recombinant or synthetic methods, or by any combination of these and similar techniques.

A "native-sequence FGF-5 polypeptide" comprises a polypeptide having the same amino acid sequence as an FGF-5 polypeptide derived from nature, with or without the native signal sequence and with or without the N-terminal methionine. Such native-sequence FGF-5 polypeptides can be isolated from nature or they can be produced by recombinant or synthetic means. The term "native-sequence FGF-5 polypeptide" specifically encompasses naturally occurring truncated forms of a polypeptide disclosed herein, naturally occurring variant forms (e.g., alternatively spliced forms), and naturally occurring allelic variants of an FGF-5 polypeptide. In one embodiment of the invention, the native-sequence FGF-5 polypeptide is a native-sequence human FGF-5 polypeptide comprising amino acid residues 1 to 248 of FIG. 8 (SEQ ID NO:3).

The term "FGF-5 variant" means an active FGF-5 polypeptide as defined below having at least at least 75% amino acid sequence identity with the amino acid sequence of the native FGF-5 molecule, more preferably at least 80%, more preferably at least 85%, even more preferably at least 90%, and most preferably at least 95% amino acid sequence identity with human FGF-5 having the deduced amino acid sequence shown in FIG. 8 (SEQ ID NO:3). Such variants include, for instance, FGF-5 polypeptides wherein one or more amino acid residues are added, or deleted, at the N- or C-terminus of the full-length amino acid sequence of FIG. 8 (SEQ ID NO:3), functional fragments or analogs of native-sequence FGF-5 having qualitative biological activity in common with the full-length FGF-5 polypeptide, including variants from other species, but excludes a native-sequence FGF-5 polypeptide. Alternatively, a variant can be a biologically active FGF-5 encoding nucleic acid which can hybridize under stringent conditions to a nucleotide enumerated above. For example, a biologically active FGF-5 variant is a polypeptide which can prevent or substantially reduce retinal neuron or photoreceptor cell death.

"Percent (%) amino acid sequence identity" with respect to the FGF-5 sequences identified herein is defined as the percentage of amino acid residues in a candidate sequence that are identical with the amino acid residues in the FGF-5 sequence, after aligning the sequences and introducing gaps, if necessary, to achieve the maximum percent sequence identity, and not considering any conservative substitutions as part of the sequence identity. The % identity values used herein may be generated by WU-BLAST-2 (Altschul et al., *Methods in Enzymology* 266: 460480 (1996)).

WU-BLAST-2 used several search parameters, most of which are set to the default values. The adjustable parameters are set with the following values: overlap span=1, overlap fraction=0.125, word threshold (T)=11. A % amino acid sequence identity value is determined by the number of matching identical residues divided by the total number of residues in the aligned region.

Polypeptide variants may come in different forms. "Substitutional" variants are those that have at least one amino acid residue in a native sequence removed and a different amino acid inserted in its place at the same position. The substitutions may be single, where only one amino acid in the molecule has been substituted, or they may be multiple, where two or more amino acids have been substituted in the same molecule. "Insertional" variants are those with one or more amino acids inserted immediately adjacent to an amino acid at a particular position in a native sequence. Immediately adjacent to an amino acid means connected to either the $\alpha$-carboxyl or $\alpha$-amino functional group of the amino acid. "Deletional" variants are those with one or more amino acids in the native amino acid sequence removed. Ordinarily, deletional variants will have one or two amino acids deleted in a particular region of the molecule. Polypeptide variants also include covalent modifications to residues in addition to epitope-tagged heterogeneous FGF-5 polypeptides.

"Percent (%) amino acid sequence identity" and "percent (%) nucleic acid sequence identity" with respect to the FGF-5 sequences identified herein is defined as the percentage of amino acid or nucleotide residues, respectively in a candidate sequence that are identical with the amino acid or nucleotide residues in an FGF-5 polypeptide sequence, after aligning the sequences and introducing gaps, if necessary, to achieve the maximum percent sequence identity, and not considering any conservative substitutions as part of the sequence identity. Alignment for purposes of determining percent amino acid or nucleotide sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For example, it will be appreciated that particular fragments or subregions of two sequences may have a greater or lesser degree of homology than a comparison between the entire fragments themselves.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends upon the ability of denatured DNA to reanneal when complementary strands are present in an environment near but below their $T^m$ (melting temperature). The higher the degree of desired homology between the probe and hybridizable sequence, the higher the relative temperature which can be used. As a result, it follows that higher relative temperatures would tend to make the reaction conditions more stringent, while lower temperatures less so. Moreover, stringency is also inversely proportional to salt concentrations. For additional details and explanation of stringency of hybridization reactions, see Ausubel et al., *Protocols in Molecular Biology* (1995).

That said, "stringent conditions" are exemplified by reaction conditions characterized by: (1) low ionic strength and high temperature for washing, for example 0.015 M sodium chloride/0.0015 M sodium citrate/0.1% sodium dodecyl sulfate at 50° C.; (2) the use of a denaturing agent, such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C. Alternatively, stringent conditions can be: 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. The skilled artisan will recognize how to adjust the temperature, ionic strength, etc. as necessary to accommodate factors such as probe length and the like.

"Isolated," when used to describe the various polypeptides disclosed herein, means polypeptide that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the FGF-5 in its natural environment will not be present. Ordinarily, however, isolated polypeptide will be prepared by at least one purification step.

"Active FGF-5" or "biological activity of FGF-5" or "FGF-5 biological activity", for purposes herein, describes form(s) of an FGF-5 polypeptide which retain the biological activity of delaying, preventing or rescuing retinal neurons, e.g., photoreceptor cells from injury, degradation or death.

"Treatment" refers to both therapeutic treatment and prophylactic or preventative measures. Those in need of treatment include those already with the disorder as well as those in which the disorder is to be prevented.

"Delaying, preventing or rescuing retinal cells from injury or death" as a result of the method of the invention refers to the ability to keep such retinal cells viable or alive for a period of time greater than is observed without application of said method. Retinal cell death can result from injury, disease or even aging. Retinal cell injury can also result in degraded cells or those having a limited capacity for normal physiological operation. The effect can be measured either in vitro with isolated retinal cells or in vivo with subjects having compromised retinal cells due to injury or disease.

"Mammal" for purposes of treatment refers to any animal classified as a mammal, including humans, domestic and from animals, and zoo, sports, or pet animals, such as dogs, horses, cats, sheep, pigs, cattle, etc. Preferably, the mammal is human.

A "disorder" is any condition that would benefit from treatment with the FGF-5 polypeptides. This includes both chronic and acute disorders, as well as those pathological conditions which predispose the mammal to the disorder in question. Non-limiting examples of disorders to be treated herein include any condition which results in injury or death of photoreceptor or other retinal cells. Examples of conditions include: retinal detachment, age-related and other maculopathies, photic retinopathies, surgery-induced retinopathies (either mechanically or light-induced), toxic retinopathies including those resulting from foreign bodies in the eye, diabetic retinopathies, retinopathy of prematurity, viral retinopathies such as CMV or HIV retinopathy related to AIDS, uveitis, ischemic retinopathies due to venous or arterial occlusion or other vascular disorder, retinopathies due to trauma or penetrating lesions of the eye, peripheral vitreoretinopathy, and inherited retinal degenerations. Exemplary retinal degenerations include e.g., hereditary spastic paraplegia with retinal degeneration (Kjellin and Barnard-Scholz syndromes), retinitis pigmentosa, Stargardt disease, Usher syndrome (retinitis pigmentosa with congenital hearing loss), and Refsum syndrome (retinitis pigmentosa, hereditary hearing loss, and polyneuropathy). Additional disorders which result in death of retinal neurons include, retinal tears, detachment of the retina and pigment epithelium, degenerative myopia, acute retinal necrosis syndrome (ARN), traumatic chorioretinopathies or contusion (Purtscher's Retinopathy) and edema.

"A therapeutically effective amount" is the an amount of active FGF-5 which is required to achieve measurable delay, rescue or prevention of damage to retinal neurons.

II. Identification of FGF-5

The description below relates primarily to production of FGF-5 polypeptide by culturing cells transformed or transfected with a vector containing at least human FGF-5 nucleic acid. It is of course contemplated that alternative methods, which are well known in the art, may be employed to prepare FGF-5 polypeptide. For example, the FGF-5 amino acid sequence, or active portions thereof, may be produced by direct peptide synthesis using solid-phase technique. Stewart et al., Solid-Phase Peptide Synthesis (W.H. Freeman Co., San Francisco, Calif. 1969); Merrifield, *J. Am. Chem. Soc.* 85: 2149–2154 (1963). In vitro protein synthesis may be performed using manual techniques or by automation. Automated synthesis may be accomplished, for example, using an Applied Biosystems peptide synthesizer (Foster City, Calif.) in accordance with the manufacturer's instructions. Various portions of FGF-5 polypeptide may be chemically synthesized separately and combined using chemical or enzymatic methods to produce a full-length FGF-5 polypeptide.

III. Recombinant production of FGF-5

FGF-5 may be purchased from any high quality laboratory reagent supply company. For example, a source is R & D systems, 614 McKinley Place, N.E., Minneapolis, Minn. 55413, cat. Number 237-F5/CF, lot number GQ 127030. Alternatively, it can be prepared in *E. coli* as described in Clements et al., *Oncogene* 8: 1311–1316 (1993). As a less preferred alternative, the procedure outlined in Haub et al., *Proc. Natl. Acad. Sci. USA* 87: 8022–8026 (1990).

The FGF-5 polypeptides of the present invention may be prepared by standard recombinant methods by culturing cells transfected to express FGF-5 nucleic acid. A typical standard method is by transforming the cells with an expression vector and recovering the polypeptide from the cells. However, it is envisioned that the FGF-5 polypeptides may be produced by homologous recombination, or by recombinant production methods utilizing control elements introduced into cells already containing DNA encoding FGF-5. For example, a promoter, enhancer element, a suppresser, or an exogenous transcription modulatory element may be inserted in the genome of the intended host cell in proximity of and in an orientation sufficient to influence the transcription of DNA encoding the desired FGF-5 polypeptide. The control element does not encode FGF-5, rather the DNA can be indigenous to the host cell genome. Next, cells can be screened for making the polypeptides of this invention, or for increased or decreased levels of expression, as desired. General techniques of recombinant DNA technology are, for example, disclosed in Sambrook et al., *Molecular Cloning: A Laboratory Manual*, 2d Edition (Cold Spring Harbor Press, Cold Spring Harbor, N.Y. (1989) and in Ausuble et al., *Current Protocols in Molecular Biology*, John Wiley and Sons, Inc. USA (1995).

Thus, the invention contemplates a method for producing FGF-5 comprising inserting into the genome of a cell containing nucleic acid encoding a FGF-5 polypeptide, a transcription modulatory element and the nucleic acid molecule. The invention also contemplates a host cell containing the indigenous FGF-5 polypeptide nucleotide operably linked to endogenous control sequences recognized by the host cell.

B. Amino Acid Variants of Native FGF-5 Proteins or Fragments

Amino acid sequence variants of native FGF-5s and functional fragments thereof may be prepared by methods known in the art by introducing appropriate nucleotide changes into a native or variant FGF-5, or by in vitro synthesis of the desired polypeptide. There are two principal variables in the construction of amino acid sequence variants: (1) the location of the mutation site and; (2) the nature of the mutation. With the exception of naturally-occurring alleles, which do not require the manipulation of the DNA sequence encoding FGF-5, the amino acid sequence variants of FGF-5 are preferably constructed by mutating FGF-5, either to arrive at an allele or an amino acid sequence variant that does not occur in nature.

Amino acid alterations can be made at sites that differ in FGF-5s from various species, or in highly conserved regions, depending on the goal to be achieved. For example, mutations which result in an enzyme with greater affinity for the FGF-5 receptors in photoreceptor cells. In addition, such variants would also be useful in the diagnosis of pathological conditions associated with the overexpression of FGF-5.

Sites of mutations will typically be modified in series, e.g., by (1) substituting first with conservative choices, and then with more radical selections depending upon the results achieved, (2) deleting the target residue or residues, or (3) inserting residues of the same or different class adjacent to the located site, or combinations of options (1)–(3).

As the third cysteine in native FGF-5 is unpaired, it may be preferable to mutate this residue to serine to assist in refolding of the protein subsequent to expression in *E. coli* or a similar prokaryote.

C. Selection and Use of a Replicable Vector

The nucleic acid (e.g. cDNA or genomic DNA) encoding native or variant FGF-5 polypeptide or functional fragment thereof is inserted into a replicable vector for further cloning (amplification of the DNA or for expression). Many vectors are available, and selection of the appropriate vector will depend on (1) whether it is to be used for DNA amplification or for DNA expression, (2) the size of the nucleic acid to be inserted into the vector, and (3) the host cell to be transformed with the vector. Each vector contains various components depending on its function (amplification of DNA or expression of DNA) and the host cell with which it is compatible. That said, the vector may take the form of a plasmid, cosmid, viral particle or phage. The appropriate nucleic acid may be inserted into the vector by a variety of procedures. In general, DNA is inserted into an appropriate restriction endonuclease site(s) using techniques known in the art. The vector components generally include, but are not limited to, one or more of the following: a signal sequence, an origin of replication, one or more marker genes, an enhancer element, a promoter, and a transcription termination sequence, each of which is described below.

Figure 7:
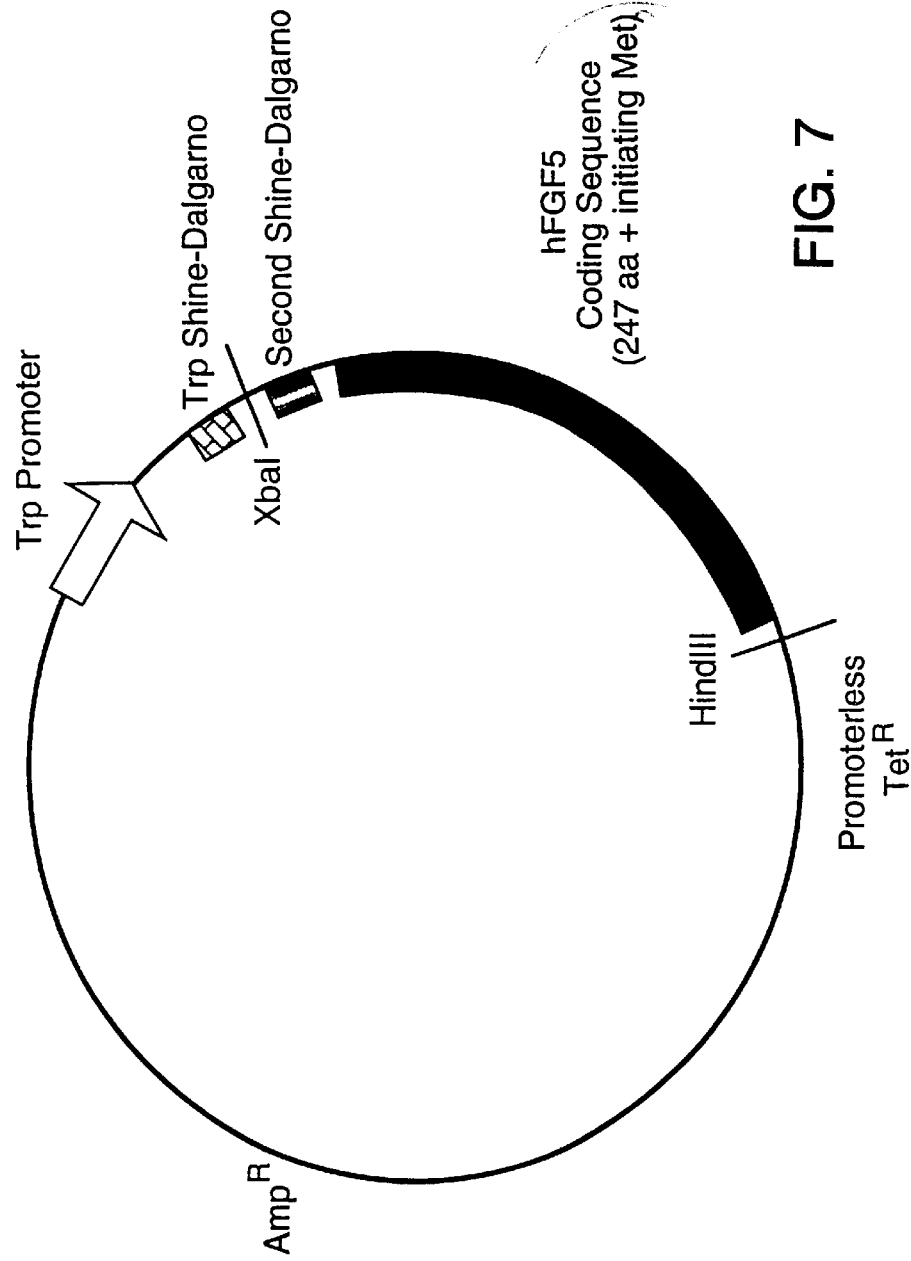
FIG. 7 is a diagram of plasmid hFGF5 *E. Coli* expression plasmid.

The preferred method of FGF-5 production is direct expression. Additional techniques exist to enhance the expression of heterologous genes in *E. coli*, such as is found in Yansura, D. & Simmons, L., *Enzymology* 4: 151–158 (1992). Preferably, the expression vector can be constructed from pBR322 [Sutcliffe, *Cold Spring Harbor Symp. Quant. Biol.* 43: 77–90 (1978)]. A Trp promoter is used to provide the transcriptional sequence required for efficient preferred expression of the FGF-5 gene in *E coli*. Yanofsky et al., *Nucleic Acids Res.* 9: 6647–6668 (1981). Two Shine-Dalgarno sequences, the Trp Shine-Dalgarno and a second Shine-Dalgarno, are used to facilitate the translation of FGF-5Yanofsky et al., supra; Ringquist et al., *Mol. Microbiol.* 6: 1219–1229 (1992). The FGF-5 coding sequence is located downstream of the promoter and Shine-Dalgarno sequences. This coding sequence is preceded by a methionine initiation codon and only codes for amino acids 1–248 of hFGF-5 (SEQ ID NO:3). A diagram of this plasmid is illustrated in FIG. 7.

D. Selection and Transformation of Host Cells (1) Host Cells

Suitable host cells for cloning or expressing the DNA in the vectors herein are the prokaryote, yeast, or higher eukaryote cells described above. Suitable prokaryotes for this purpose include eubacteria, such as Escherichia, e.g., *E. coli*, Enterobacter, Erwinia, Klebsiella, Proteus, Salmonella, e.g., *Salmonella typhimurium*, Serratia, e.g., *Serratia marcescans*, and Shigella, as well as Bacilli such as *B. Subtilis* and *B. Licheniformis* (e.g., *B. Licheniformis* 41P disclosed in DD 266,710 published Apr. 12, 1989), Pseudomonas such as *P. aeruginosa, Salmonella typhimurium*, or *Serratia marcescans* and Streptomyces. The preferred strains have and impaired heat shock response and contain protease deletions and mutations. For example, the strain 44C6, which is a derivative of W3110 (ATCC 27,325) having the genotype fhuAΔ (tonAΔ) lonΔ galE rpoHts (htpRts) ΔclpP. Another secretion strain which may be used is 27C7 (ATCC 55,244). Other *E. coli* cloning hosts include, for example, *E. coli* 294 (ATCC 31,446), *E. coli* B and *E. coli* X1776 (ATCC 31,537).

(2) Culturing the Host Cells

Prokaryotic cells used to produce the FGF-5s of this invention may be cultured in suitable media as described generally in Sambrook et al., supra and Ausubel et al., supra. Briefly, the transformed cells are grown at 30° C. or 37° C. until the optical density (measured at 550 nm) reaches about 2–3. The culture diluted into a production medium, regrown with aeration, and 3-β-Indole acrylic acid (IAA) is added. Growth is continued with aeration for about another 15 hours after which time the cells are harvested by centrifugation. When refolding is necessary, the procedure outlines under F. Isolation, Purification and Refolding of FGF-5, below, may be employed.

More specifically, a 10 liter fermentation may be carried out as follows. The fermentor is first sterilized with a sterilization solution of about 5–6.5 liters of deionized water to which is added: ammonium sulfate (50.0 g); potassium phosphate, dibasic (60.0 g); sodium phosphate, monobasic dihydrate (30.0 g); sodium citrate, dihydrate (10.0 g); 1-isoleucine (5 g); 25% aq. soln. of pluronic polyol L-61 (BASF, antifoam). After the fermentor vessel cools down, the growth media is added. The growth media after inoculation has a volume typically of about 8.5 liters. The media components are comprised of: 50% glucose solution (15 mL); 1M magnesium sulfate (70 mL); 20% Hycase solution (250 mL); 20% yeast extract solution (250 mL); 2 mg/mL ampicillin (250 mL) and trace metals (5 mL). A typical 1L trace metal solution is composed of the following: HCl (100 mL); Ferric chloride hexahydrate (27 g); Zinc sulphate heptahydrate (8 g); Cobalt Chloride hexahydrate (7 g); Sodium molybdate (7 g); Cupric sulphate pentahydrate (8 g); boric acid (2 g); Manganese sulphate monohydrate (5 g); distilled water (total volume to 1 L). Inoculation is made with 500 mL of an 18–20 hour LB culture grown in the presence of ampicillin, and the fermentor is agitated at 750 rpm and aerated at 10 slpm. The culture pH is maintained at 7.0 by automatic addition of ammonium hydroxide and the temperature is maintained at 30° C. When the initial glucose in the culture is exhausted, a glucose feed is started and maintained at a rate sufficient to sustain growth but not accumulate in the medium. Culture growth is monitored by measuring the optical density (O.D.) at 550 nm. When the culture O.D. reaches 25–35, 25 mL of a 25 mg/mL solution of IAA is added and the cell paste harvested after 14–18 hours of centrifugation.

(3) Detecting Gene Amplification/Expression

Gene amplification and/or expression may be measured in a sample directly, for example, by conventional Southern blotting, northern blotting to quantitate the transcription of mRNA (Thomas, *Proc. Natl. Acad. Sci. USA* 77: 5201–5205 (1980), dot blotting (DNA analysis), or in situ hybridization, using an appropriately labeled probe, based on the sequences provided herein. Various labels may be employed, most commonly radioisotopes, particularly $^{32}$P. However, other techniques may also be employed, such as using biotin-modified nucleotides for introduction into a polynucleotide. The biotin then serves as the site for binding to avidin or antibodies, which may be labeled with a wise variety of labels, such as radionuclides, fluorescers, enzymes, or the like. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of tissue sections and assay of cell culture or body fluids, to quantitate directly the expression of gene product. With immunohistochemical staining techniques, a cell sample is prepared, typically by dehydration and fixation, followed by reaction with labeled antibodies specific for the gene product coupled, where the labels are usually visually detectable, such as enzymatic labels, fluorescent labels, luminescent labels, and the like. A particularly sensitive staining technique suitable for use in the present invention is described by Hsu et al., *Am. J. Clin. Path.* 75: 734–738 (1980).

Antibodies useful for immunohistochemical staining and/or assay of sample fluids may be either monoclonal or polyclonal, and may be prepared in any mammal. Conveniently, the antibodies may be prepared against an FGF-5 mutant polypeptide or against a synthetic peptide based on the DNA sequences provided herein as described further below.

E. FGF-5 Polypeptide Purification

FGF-5 preferably is recovered from host cell lysates when directly expressed without a secretory signal, although it may also be recoverable from the culture media as a secreted polypeptide. If membrane-bound, it can be released from the membrane using a suitable detergent solution (e.g., Triton-X 100) or by enzymatic cleavage. Cells employed in expression of FGF-5 polypeptides can be disrupted by various physical or chemical means, such as freeze-thaw cycling, sonication, mechanical disruption, or cell lysing agents.

When using recombinant techniques, the FGF-5 polypeptide can be produced intracellularly, in the periplasmic space, or directly secreted into the medium. If the FGF-5 is produced intracellularly, it will usually be necessary to purify FGF-5 from other recombinant cell proteins or polypeptides to obtain preparations that are substantially homogenous to the FGF-5As a first step, the culture medium or lysate is centrifuged to remove the particulate debris, e.g. host cells or lysed fragments. A procedure is described in Carter et al., *Bio/Technology* 10: 163–167 (1992) for isolating proteins which are secreted to the periplasmic space of *E. coli*. Briefly, cell paste is thawed in the presence of sodium acetate (pH 3.5), EDTA, and phenylmethylsulfonylfluoride (PMSF) over about 30 minutes. Cell debris can be removed by centrifugation.

Many heterogeneous proteins expressed in *E. coli* require refolding in order to impart activity. When this is necessary, the following procedure can be used. For a general discussion of procedures suitable for refolding of recombinant or synthetic FGF-5, include any N- or C-terminal extended forms, the reader is referred to the following patents: Builder et al., U.S. Pat. No. 4,511,502; Jones et al., U.S. Pat. No. 4,512,922; Olson, U.S. Pat. No. 4,518,526; Builder et al., U.S. Pat. No. 4,620,948.

(i) Recovery of Non-soluble FGF-5

A microorganism such as *E. coli* which is expressing FGF-5 encoded by any suitable plasmid is fermented under conditions in which FGF-5 is deposited in insoluble "refractile bodies". Optionally, cells are first washed in a cell disruption buffer. Typically, about 100 g of cells are resuspended in about 10 volumes of a cell disruption buffer (e.g. 10 mM Tris, 5 mM EDTA, pH 8) with, for example, a Polytron homogenizer, followed by centrifugation at 5000×g for 30 minutes. Cells are then lysed using any conventional technique such as tonic shock, sonication, pressure cycling, chemical or enzymatic methods. For example, the washed cell pellet above may be resuspended in another 10 volumes of a cell disruption buffer with a homogenizer and the cell suspension is passed through an LH Cell Disrupter (LH Inceltech, Inc.) or through a Microfluidizer® (Microfluidics Int'l) according to the manufacturer's instructions. The particulate matter containing FGF-5 is then separated form the liquid phase and optionally washed with any suitable liquid. For example, a suspension of cell lysate may be centrifuged at 5,000×g for 30 minutes, resuspended and optionally centrifuged a second time to make a washed refractile body pellet. The washed pellet may be used immediately or optionally stored frozen (at e.g. -70° C.).

(ii) Solubilization and Purification of Monomeric FGF-5

Insoluble FGF-5 polypeptide in the refractile body is then solubilized with a solubilizing buffer. The solubilizing buffer contains a chaotropic agent and is usually buffered at a basic pH and contains a reducing agent to improve the yield of monomeric FGF-5 Representative chaotropic agents include urea, guanidine-HCl, and sodium thiocyanate. A preferred chaotropic agent is guanidine-HCl. The concentration of chaotropic agent is usually 4–9 M, preferably 6–8 M. The pH of the solubilizing buffer is maintained by any suitable buffer in a pH range of from about 7.5–9.5, preferably 8.0–9.0, and most preferably 8.0. Preferably, the solubilizing buffer also contains a reducing agent to aid formation of the monomeric form of FGF-5. Suitable reducing agents include organic compounds containing a free thiol (RDH). Representative reducing agents include dithiothreitol (DTT), dithioerythritol (DTE), mercaptoethanol, glutathione (GSH), cysteamine and cysteine. A preferred reducing agent is dithiothreitol (DTT). Optionally, the solubilizing buffer may contain a mild oxidizing agent (e.g. molecular oxygen) and a sulfite salt to form monomeric mutant FGF-5 via sulfitolysis. In this embodiment, the resulting [FGF-5]-S-sulfonate is later refolded in the presence of redox buffer (e.g., GSH/GSSG) to form the properly folded FGF-5.

The FGF-5 protein is usually further purified using, for example, centrifugation, gel filtration chromatography and reversed phase column chromatography.

By way of illustration, the following procedure has produced suitable yields of monomeric FGF-5. The refractile body pellet is resuspended in about 5 volumes by weight of the solubilizing buffer (20 mM Tris, pH 8, with 6–8 M guanidine and 25 mM DTT) and stirred for 1–3 hr., or overnight at 4° C. to effect solubilization of the mutant FGF-5 protein. High concentrations of urea (6–8M) are also useful but generally result in somewhat lower yields compared to guanidine. After solubilization, the solution is centrifuged at 30,000×g for 30 min. to produce a clear supernatant containing denatured, monomeric FGF-5. The supernatant is then chromatographed on a Superdex® 200 gel filtration column (Pharmacia, 2.6×60 cm) at a flow rate of 2 ml/min. and the protein eluted with 20 mM Na phosphate, pH 6.0, with 10 mM DTT. Fractions containing monomeric, denatured FGF-5 eluting between 160 ml and 200 ml are pooled. The FGF-5 protein is further purified on a semi-preparative C4 reversed phase column (2×20 cm VYDAC). The sample is applied at 5 ml/min. to a column equilibrated in 0.1% TFA (trifluoroacetic acid) with 30% acetonitrile. The protein is eluted with a linear gradient of acetonitrile (30–60% in 60 min.). The purified reduced protein elutes at approximately 50% acetonitrile. This material is used for refolding to obtain biologically active FGF-5.

(iii) Refolding of FGF-5 to Generate the Biologically Active Form

Following solubilization and further purification of FGF-5, the biologically active form is obtained by refolding the denatured monomeric FGF-5 in a redox buffer. Depending upon the potency of the FGF-5, it may be possible to obtain biologically active material utilizing many different buffer, detergent and redox conditions. However, under most conditions, only a small amount of properly folded material (<10%) is obtained. For commercial manufacturing processes, it is desirable to have refolding yields at least 10%, more preferably 30–50% and most preferably >50%. Many different detergent including Triton X-100, dodecyl-beta-maltoside, CHAPS, CHAPSO, SDS, sarkosyl, Tween 20 and Tween 80, Zwittergent 3–14 and others may be used to produce at least minimal folding. However, the most preferred detergents are of the CHAPS family (CHAPS and CHAPSO) which appear to work best in refolding and limit protein aggregation and improper disulfide formation. Levels of CHAPS greater than about 1% are most preferred. To optimize yields, it is preferred to have sodium chloride present (0M–0.5M). It is further preferred to have EDTA (1–5 mM) in the redox buffer in order to limit the amount of metal-catalyzed oxidation (and aggregation). At least 15% glycerol is further preferred in order to reach optimal refolding conditions. For maximum yields, it is further preferred that the redox buffer have both an oxidized and reduced organic thiol (RSH). Suitable redox pairs include mercaptoethanol, glutathione (GSH), cysteamnine, cysteine and their corresponding oxidized forms. Preferred redox are glutathione (GSH):oxidized glutathione (GSSG) or cysteine:cystine. The most preferred redox pair is glutathione (GSH):oxidized glutathione (GSSG). Generally higher yields are observed when the mole ratio of oxidized member of the redox pair is equal to or in excess over the reduced member of the redox pair. pH values between 7.5 and about 9 are optimal for refolding of FGF-5 polypeptides. Organic solvents (e.g. ethanol, acetonitrile, methanol) were tolerated at concentrations of 10–15% or lower. Higher levels of organic solvents increased the amount of improperly folded forms. Tris and phosphate buffers were generally useful. Incubation at 4° C. also produced higher levels of properly folded FGF-5

Refolding yields of 40–60% (based on the amount of reduced and denatured FGF-5 used in the refolding reaction) are typical for preparations of FGF-5 that have been purified through the first C4 step. Active material can be obtained when less pure preparations (e.g. directly after the Superdex® 200 column or after the initial refractile body extraction) although the yields can be less due to precipitation and interference of non-FGF-5 proteins during the FGF-5 refolding process.

Since FGF-5 has three cysteine residues, it is possible to generate three different disulfide versions of this protein:

version 1: disulfides between cysteine residues 1 & 2;

version 2: disulfides between cysteine residues 1 & 3;

version 3: disulfides between cysteine residues 2 & 3;

In order to assist in achieving optimal results during refolding, it may become necessary to mutate the third cysteine so as to ensure formation of the disulfide bond between the first and second cysteines.

During the initial exploration in determining refolding conditions, different peaks containing the FGF-5 protein can be separated by C4 reverse phase chromatography. Upon testing for the peak with the most significant biological activity, conditions may be optimized to yield preferentially for that version.

The disulfide pattern for the native sequence FGF-5 (e.g., SEQ ID NO:2, SEQ ID NO:3, SEQ ID NO:5) has been determined to be between cysteine residues 1 and 2.

IV. THERAPEUTIC INDICATIONS

Various disorders can result in death of retinal neurons. These include such widely disparate conditions as detachment of the retina and pigment epithelium, degenerative myopia, acute retinal necrosis syndrome (ARN), and traumatic chorioretinopathies or contusion (Purtscher's Retinopathy). Retinal tears is a condition characterized by where the retina tears or separates from the underlying choroid, which can sometimes result in rupturing of the choroid. Retinal tears may occur for a wide variety of reasons. Particularly troublesome are macular holes which produce blurred central vision or metamorphopsia.

While the direct cause of most macular holes is unknown, they have been associated with trauma, cystic degeneration and vitreoretinal traction. Also, full thickness macular holes have appeared following myopic degeneration, laser photocoagulation, lightning strike and pilocarpine administration. Macular holes are also present in high frequency after cataract extraction. A particular form of acute macular holes is idiopathic senile macular hole, which involves a full thickness hole through the macula surrounded by annular retinal detachment. It is believed that macular holes begin with central or foveolar detachment, which then eventually develops into a full-depth macular hole. Gass et al. (1988), *Arch. Ophthalmol.* 106: 629–639. While surgical procedures, such as trans-para plana vitrectomy may interrupt the progress of macular degeneration to a full blown macular hole, this operation can permanently damage central vision, and typically only improves vision 40% of the time.

Other retinal disorders which can result in photoreceptor cell death include edema, ischemic conditions and uveitis. Macular and retinal edema are often associated with metabolic illnesses such as diabetes mellitus. Retinal edema is found in a large percentage of individuals who have undergone cataract extraction and other surgical procedures upon the eye. Edema is also found with accelerated or malignant hypertension. Macular edema is a common complication of prolonged inflammation due to uveitis, Eales disease, or other diseases. Local edema is associated with multiple cystoid bodies ("cotton bodies") as a result of AIDS.

Retinal ischemia can occur from either choroidal or retinal vascular diseases, such as central or branch retinal vision occlusion, collagen vascular diseases and thrombocytopenic purpura. Retinal vasculitis and occlusion is seen with Eales disease and systemic lupus erythematosus.

Age-related macular degeneration (AMD) is the major cause of severe visual loss in United States citizens over the age of 55. AMD may occur either in an atrophic or exudative form. Most AMD patients have a build up of deposits within and under the retinal pigment epithelium in the macular region resulting in atrophy of the retina and the retinal pigment epithelium. The retinal pigment scavenge for photoreceptor discs from the rods and cones for years and accumulate intracellular wastes. The incompletely digested residues reduce cytoplasmic space and interfere with metabolism. Feeny-Burns, et al., *Invest Ophthal. Mol. Vis. Sci.* (1984), 25: 195–200. As the cell volume available to the organelles diminishes, the capacity to digest photoreceptors decreases, which may be the basis for macular degeneration.

Exudative AMD is characterized by the growth of blood vessels from the choriocapillaris through defects in Bruch's membrane, and in some cases the underlying retinal pigment epithelium (RPE). The accumulation of serous or hemorrhagic exudates escaping from these vessels results in fibrous scarring of the macular region with attendant degeneration of the neuroretina and permanent loss of central vision. Exudative AMD has also been associated with choroidal neovascularization, detachment and tears of the retinal pigment epithelium. The cascade retinal events is responsible for more than 80% of cases of significant visual loss in patients with AMD.

Laser photocoagulation has been attempted in an effort to ameliorate the initial or recurrent neovascular lesions associated with AMD. *Arch. Ophthalmol.* (1991) 109: 1220; *Arch. Ophthalmol.* (1991) 109: 1232; *Arch. Ophthalmol.* (1991)109:1242. Unfortunately, AMD patients with subfoveal lesions subjected to laser treatment experienced a severe reduction in visual acuity (mean 3 lines) at 3 months follow-up. Moreover, at two years post-treatment treated eyes had only marginally better visual acuity than their untreated counterparts (means of 20/320 and 20/400, respectively). Another drawback of the procedure is that vision immediately after surgery is worse.

As a result, the retinal neuron survival agents of the present invention are promising candidates for the treatment of retinal tears, degenerative myopia, acute retinal necrosis syndrome (ARN), and traumatic chorioretinopathies or contusion (including Purtscher's retinopathy), macular holes, macular degeneration (including age-related macular degeneration or AMD), edema, ischemic conditions (e.g., central or branch retinal vision occlusion, colagen vacuolar diseases, thrombocytompenic purpura), uveitis and retinal vasculitis and occlusion associated with Eales disease and systemic lupus erythematosus.

V. MODES FOR CARRYING OUT THE INVENTION

A. Retinal Neuron (including photoreceptor) Survival Assays:

In these assays, neural retinas are removed from pigment epithelium and dissociated into a single cell suspension using 0.25% trypsin in $Ca^{2+}$, $Mg^{2+}$-free PBS. The cells are then plated out in 96-well plates at 100,000 cells per well in DMEM/F12 supplemented with N2. After 2–3 days in culture, the cells are fixed and stained. Since death typically occurs upon detachment of neural retinal cells from the underlying pigment epithelium the relative survival enhancing effect of the tested agent can be readily determined by comparison with the untreated control wells.

The procedure is described in greater detail in the examples.

B. Age-related Macular Degeneration (AMD):

In this assay, the effectiveness and safety of locally administered FGF-5 is examined using a procedure substantially similar to that outlined in WO 94/01124, filed Jul. 8, 1993 which describes subretinal or intravitreal injections of retinal survival promoting therapeutic agents. Briefly, patients with visual acuity of 20/160 or better with a recent diagnosis of AMD are examined for change in visual acuity from baseline and stabilization. Study parameters should measure best corrected visual acuity for both distance and near vision, intraocular pressure, lens status and refraction. The amount of serous and hyperfluorescence from classic/occult neovascularization, total lesion size and foveal involvement are also measured on fluorescein angiography and ICG (indocyanine green) angiography.

C. Macular Holes:

In this assay, the safety and effectiveness of locally administered FGF-5 is examined using a procedure substantially similar to that outlined in WO 94/01124, filed Jul. 8, 1993 which describes subretinal or intravitreal injection of retinal survival promoting therapeutic agents. Briefly, patients with confirmed macular holes are examined for visual acuity and analyzed by intraocular pressure, fundus photographs, and fluorescein angiography.

The rational for treatment is to induce the flattening of the edges of the macular hoes in order to resolve retinal detachment and thickening surrounding the hole. It is believed that a reduction in the traction force which elevates the retina around the hole coupled with and induction of the chorioretinal adhesion along the edge of the hole is necessary for therapeutic effect. The procedure is described in more detail in the examples.

D. Light-induced Photoreceptor Injury:

In this assay, an albino rat is maintained in first a cyclic light environment followed by exposure to a constant light source with and without administration of the tested photoreceptor survival agent. The intravitreal administration of factors into the eyes of albino rats enables the assessment of both the ability of the factors to rescue photoreceptors from degeneration as well as the side effects, such as incidence of macrophages, associated with each factor.

Briefly, rats are given intraocular injections prior to constant light exposure and compared to control animals who received sham and no injections. Subsequent to constant light exposure, the eyes are removed, embedded in epoxy resin and sectioned along the vertical meridian. The degree of light-induced retinal degeneration can be measured first by examining the outer nuclear layer thickness and second by a subjective score assigned to the relative integrity of the retina.

E. Light Ablation:

In this assay, the degree of photoreceptor rescue is measured in female Sprague-Dawley rats in a modification of the procedure described in Reme et al., *Degen. Dis. Retina*, Ch. 3, Ed. R. E. Anderson et al., Plenum Press, New York (1995). Briefly, animals are first acclimated to cyclical lighting, followed by immersion in total darkness. Animals are injected with test factor prior to intermittent light exposure. The degree of retinal degeneration or survival promoting activity of the tested factors is reported as the thickness of the photoreceptor cell layer or number of TUNEL labeled photoreceptor cell nuclei.

F. Corneal Pocket Assay:

In this assay, particular agents are tested to determine whether they are angiogenic under a procedure adapted from Polverini et al., *Methods Enzymol.* 198: 440–450 (1991). Briefly, Sprague-Dawley are anesthetized, secured and an incision is made in their corneas into which is placed a pellet of the test factor in combination with sucralfate and Hydron.

G. Vascular Endothelial Cell Mitogenicity Assay:

This particular assay measures the mitogenicity (e.g., angiogenesis) of the test factor on vascular endothelial cells. It was developed as a reliable means of measuring the purification of bFGF (SEQ ID NO:4) as described by Ferrara, et al., *Methods of Enzymology* 198: 391–405 (1991). Briefly, bovine adrenal cortex-derived cells are grown and maintained in culture in the presence of low glucose DMEM, the test factor is administered and test cultures vs. controls are measured.

H. Administration Methods:

The FGF-5 polypeptides of the present invention can be delivered to the eye through a variety of routes. Methods of introduction include any mode of administration known in the art, including but not limited to intravenously, intraarterially, intrathecally, subcutaneously, intradermally, by injection into involved tissue, intranasally, intramuscularly, intraperitoneally, orally, or via an implanted device. They may be delivered intraocularly, by topical application to the eye or by intraocular injection into, for example the vitreous or subretinal (interphotoreceptor) space. Alternatively, they may be delivered locally by insertion or injection into the tissue surrounding the eye. They may be delivered systemically through an oral route or by subcutaneous, intravenous or intramuscular injection. Alternatively, they may be delivered by means of a catheter or by means of an implant, wherein such an implant is made of a porous, non-porous or gelatinous material, including membranes such as silastic membrane or fibers, biodegradable polymers, or proteinaceous material. The factors may be administered prior to the onset of the condition, to prevent its occurrence, for example, during surgery on the eye, or immediately after the onset of the pathological condition or during the occurrence of an acute or protracted condition.

Intravitreal injection of potential retinal neuron survival promoting factors has several advantages over systemic applications. The amount of any specific agent that reaches the retina can be more accurately determined, since the eye is a round, relatively contained structure and the agent is injected directly into it. Moreover, the amount of agent that needs to be injected is minuscule compared to systemic injections. For example, a single microliter in volume (about 1 microgram of agent) is used for intravitreal injection, as compared to one to several milliliters (ten to several hundred milligrams of agent) necessary for systemic injections. In addition, the intravitreal route of administration avoids the potentially toxic effect of some agents.

Further, it may be desirable to administer the pharmaceutical compositions of the invention locally to the area in need of treatment, this may be achieved by, for example, local infusion during surgery, by injection, by means of a catheter, or by means of an implant, wherein such implant can be of a porous, non-porous, or gelatinous material, including membranes, such as silastic membranes or fibers.

The factors of the present invention may be modified to enhance their ability to penetrate the blood-retinal barrier. Such modification may include increasing their lipophilicity by, for example, glycosylation, or increasing their net charge by methods known in the art.

The factors may be delivered alone or in combination, and may be delivered along with a pharmaceutically acceptable vehicle. Ideally, such a vehicle would enhance the stability and/or delivery properties. The invention also provides for pharmaceutical compositions containing the active factor or fragment or derivative thereof, which can be administered using a suitable vehicle such as liposomes, microparticles or microcapsules. In various embodiments of the invention, it may be useful to use such compositions to achieve sustained release of the active component.

I. Pharmaceutical Compositions and Dosages

Therapeutic formulations of the polypeptide or antibody are prepared for storage as lyophilized formulations or aqueous solutions by mixing the polypeptide having the desired degree of purity with optional "pharmaceutically-acceptable" or "physiologically-acceptable" carriers, excipients or stabilizers typically employed in the art (all of which are termed "excipients"). For example, buffering agents, stabilizing agents, preservatives, isotonifiers, non-ionic detergents, antioxidants and other miscellaneous additives. (See *Remington's Pharmaceutical Sciences*, 16th edition, A. Osol, Ed. (1980)). Such additives must be nontoxic to the recipients at the dosages and concentrations employed.

Buffering agents help to maintain the pH in the range which approximates physiological conditions. They are preferably present at concentration ranging from about 2 mM to about 50 mM. Suitable buffering agents for use with the present invention include both organic and inorganic acids and salts thereof such as citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium glyconate mixture, etc.), oxalate buffer (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additionally, there may be mentioned phosphate buffers, histidine buffers and trimethylamine salts such as Tris.

Preservatives are added to retard microbial growth, and are added in amounts ranging from 0.2%–1% (w/v). Suitable preservatives for use with the present invention include phenol, benzyl alcohol, meta-cresol, methyl paraben, propyl paraben, octadecyldimethylbenzyl ammonium chloride, benzalconium halides (e.g., chloride, bromide, iodide), hexamethonium chloride, alkyl parabens such as methyl or propyl paraben, catechol, resorcinol, cyclohexanol, and 3-pentanol.

Isotonicifiers sometimes known as "stabilizers" are present to ensure isotonicity of liquid compositions of the present invention and include polyhydric sugar alcohols, preferably trihydric or higher sugar alcohols, such as glycerin, erythritol, arabitol, xylitol, sorbitol and mannitol. Polyhydric alcohols can be present in an amount between 0.1% to 25% by weight, preferably 1% to 5% taking into account the relative amounts of the other ingredients.

Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc., organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur containing reducing agents, such as urea, glutathione, thioctic acid, sodium thioglycolate, thioglycerol, $\alpha$-monothioglycerol and sodium thio sulfate; low molecular weight polypeptides (i.e. <10 residues); proteins such as human serum albumin, bovine serum albumin, gelatin or immunoglobulins; hydrophilic polymers, such as polyvinylpyrrolidone monosaccharides, such as xylose, mannose, fructose, glucose; disaccharides such as lactose, maltose, sucrose and trisaccacharides such as raffinose; polysaccharides such as dextran. Stabilizers can be present in the range from 0.1 to 10,000 weights per part of weight active protein.

Non-ionic surfactants or detergents (also known as "wetting agents") are present to help solubilize the therapeutic agent as well as to protect the therapeutic protein against agitation-induced aggregation, which also permits the formulation to be exposed to shear surface stressed without causing denaturation of the protein. Suitable non-ionic surfactants include polysorbates (20, 80, etc.), polyoxamers (184, 188 etc.), Pluronic® polyols, polyoxyethylene sorbitan monoethers (Tween®-20, Tween®-80, etc.). Non-ionic surfactants are present in a range of about 0.05 mg/ml to about 1.0 mg/ml, preferably about 0.07 mg/ml to about 0.2 mg/ml.

Additional miscellaneous excipients include bulking agents, (e.g. starch), chelating agents (e.g. EDTA), antioxidants (e.g., ascorbic acid, methionine, vitamin E), and cosolvents.

The formulation herein may also contain more than one active compound as necessary for the particular indication being treated, preferably those with complementary activities that do not adversely affect each other. For example, it may be desirable to further provide an immunosuppressive agent. Such molecules are suitably present in combination in amounts that are effective for the purpose intended.

The active ingredients may also be entrapped in microcapsule prepared, for example, by coascervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences*, 16th edition, A. Osal, Ed. (1980).

The formulations to be used for in vivo administration must be sterile. This is readily accomplished, for example, by filtration through sterile filtration membranes.

Sustained-release preparations may be prepared. Suitable examples of sustained-release preparations include semi-permeable matrices of solid hydrophobic polymers containing the antibody mutant, which matrices are in the form of shaped articles, e.g., films, or microcapsules. Examples of sustained-release matrices include polyesters, hydrogels (for example, poly(2-hydroxyethyl-methacrylate), or poly (vinylalcohol)), polylactides (U.S. Pat. No. 3,773,919), copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(–)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

The amount of therapeutic polypeptide, antibody or fragment thereof which will be effective in the treatment of a particular disorder or condition will depend on the nature of the disorder or condition, and can be determined by standard clinical techniques. Where possible, it is desirable to determine the dose-response curve and the pharmaceutical compositions of the invention first in vitro, and then in useful animal model systems prior to testing in humans. However, based on common knowledge of the art, a pharmaceutical composition effective in promoting the survival of sensory neurons may provide a local therapeutic agent concentration of between about 5 and 20 ng/ml, and, preferably, between about 10 and 20 ng/ml. In an additional specific embodiment of the invention, a pharmaceutical composition effective in promoting the growth and survival of retinal neurons may provide a local therapeutic agent concentration of between about 10 ng/ml and 100 ng/ml.

In a preferred embodiment, an aqueous solution of therapeutic polypeptide, antibody or fragment thereof is administered by subcutaneous injection. Each dose may range from about 0.5 μg to about 50 μg per kilogram of body weight, or more preferably, from about 3 μg to about 30 μg per kilogram body weight.

The dosing schedule for subcutaneous administration may vary form once a week to daily depending on a number of clinical factors, including the type of disease, severity of disease, and the subject's sensitivity to the therapeutic agent.

FGF-5 protein, peptide fragment, or variant may comprise an amino acid sequence or subsequence thereof as indicated in FIG. 8 (SEQ ID NO:3), active amino acid sequence derived therefrom, or functionally equivalent sequence (e.g. residues 22 to 268 of SEQ ID NO:2), as this subsequence is believed to comprise the functional portion of the FGF-5 molecule.

The amount of FGF-5 protein which will be effective in the treatment of a particular disorder or condition will depend on the nature of the disorder or condition, and can be determined by standard clinical techniques. Where possible, it is desirable to determine the dose-response curve and the pharmaceutical compositions of the invention first in vitro, and then in useful animal model systems prior to testing in humans. However, based on common knowledge of the art, a pharmaceutical composition effective in promoting the survival of sensory neurons may provide a local FGF-5 protein concentration of between about 10 and 1000 ng/ml, preferably between 100 and 800 ng/ml and most preferably between about 200 ng/ml and 600 ng/ml of FGF-5. In an additional specific embodiment of the invention, a pharmaceutical composition effective in promoting the growth and survival of retinal neurons may provide a local FGF-5 protein concentration of between about 10 ng/ml and 1000 ng/ml.

The dosing schedule for subvitreous administration of FGF-5 may vary from once a week to daily depending on a number of clinical factors, including the type of disease, severity of disease, and the subject's sensitivity to FGF-5. Nonlimiting examples of dosing schedules are 3 μg/kg administered twice a week, three times a week or daily, a dose of 7 μg/kg twice a week, three times a week or daily, a dose of 10 μg/kg twice a week, three times a week or daily.

Effective doses of additional neurotrophic factors administered in combination with FGF-5, such CNTF are in the same dose ranges as the effective dose of FGF-5 described herein. The active compound of the present method, FGF-5, may optionally be formulated with a second agent, such as a neurotrophic factor. Exemplary neurotrophic factors include: nerve growth factor (NGF), aGF, ciliary neurotrophic factor (CNTF), bovine-derived neurotrophic factor (BDNF), neurotrophin-3 (NT-3), neurotrophin-4 (NT-4), aFGF, IL-1β, TNFα, Insulin-like growth factor (IGF-1, IGF-2), transforming growth factor beta (TGF-β, TGF-β1) or skeletal muscle extract, may be administered in any sterile biocompatible pharmaceutical carrier, including, but not limited to, saline, buffered saline, dextrose, and water. However, certain factors such as bFGF-5, CNTF or IL-1β should be employed cautiously, as these agents may cause undesirable retinal complications such as macrophage proliferation, disorganization or the retinal structure, cell proliferation or inflammation.

If the subject manifests undesired side effects such as temperature elevation, cold or flu-like symptoms, fatigue, etc., it may be desirable to administer a lower dose at more frequent intervals. One or more additional drugs may be administered in combination with FGF-5 to alleviate such undesired side effects, for example, an anti-pyretic, anti-inflammatory or analgesic agent.

V. Assay Characterizations: Correlation Between in vitro Assays and in vivo Therapeutic Effect Recent studies using agarose gel electrophoresis and terminal dUTP nick-end labeling (TUNEL) indicate that photoreceptor cell death occurs principally by apoptosis. Chang, G-Q, Hao Y., Wong F. (1993), *Neuron* 11: 595–605; Portera-Cailliau, C. et al. (1993), *Proc. Nat'l Acad. Sci. USA* 91: 974–97; Adler R., *Curr. Top. Dev. Biol.* (1980) 16: 207–252. These studies examined mouse models of human retinal degeneration (retinitis pigmentosa): rd mice (which have a mutation in the b subunit of cGMP phosphodiesterase); rds mice (which have a mutation in peripherin); and transgenic mice, which have a mutation in rhodopsin. In all three models there is a substantial increase in apoptosis at the time of photoreceptor cell death. Apoptosis is also known to be prominent in the RCS rat, as well as in the light-damaged rat retina. Tso M, et al., *Invest. Opththalmol. Vis. Sci.* (1994) 35: 2693–2699; Shahinfar S., et al., *Curr. Eye Res.* (1991) 10: 47–59.

Apoptosis appears to be a tightly controlled "shutdown" process or self-selecting cell suicide which by preventing the leakage of destructive enzymes, allows healthy neighboring cells to continue their normal functioning. Wong, F., *Arch. Ophthalmol.* 113: 1245–47 (1995). During this process, the cell's outer membrane remains intact as the cell undergoes nuclear condensation, cytoplasmic shrinkage, membrane blebbing, formation of apoptotic bodies, and sometimes DNA fragmentation.

Apoptosis is now believed to play a key role in degenerative diseases of the eye, such as retinitis pigmentosa. RP is believed to be caused by mutations in the rhodopsin gene, Dryja, TP, *Nature* (1990) 343: 364–366. In addition, other photoreceptor-specific genetic mutations have been uncovered which induce RP, among them the mutants known as retinal degeneration (rd), McLaughlin M E, et al. *Nat. Genet.* (1993), 4: 30–134, and retinal degeneration slow (rds), Farrar G. J. et al., *Nature* (1991), 354: 478–80; Kajiwara K. et al., *Nature* (1991), 354: 480–83. It has further been discovered that the autosomal dominant types of RP may be caused by any one of more than 70 mutations of the rhodopsin gene. Humphries, P. et al., *Science* (1992), 256: 804–808; Dryja, T. P et al., *Invest. Ophthalmol. Vis. Sci.* (1995), 36: 1197–1200. Rhodopsin mutations are known to be the basis of autosomal recessive RP in some families as well. Rosenfeld, P. J. et al., *Nat. Genet.* (1992), 1: 209–13; Kumaramanickavel, G. et al., (1994), 8:10–11. As a result, the rhodopsin gene is now considered an archetypal model for the study of RP.

The role of apoptosis in RP has been observed in mouse photoreceptors. Several lines of transgenic mice which express mutant rhodopsin have been created, and as a result, can simulate a form of the autosomal dominant RP found in humans. These animal models exhibit dying photoreceptors through various characteristics of apoptosis, including morphological changes and DNA fragmentation. Chang C-G et al., *Neuron* (1993), 11: 595–605; Portera-Cailliau C. et al, *Proc. Natl. Acad. Sci. USA* (1994), 91: 974–978. Along with other experimental results, these findings have led researches to the conclusion that apoptosis is a major mechanism of murine photoreceptor death, as it is induced not only by mutations in the rhodopsin gene, but also by mutations in the rd and rds genes. Chang C-G et al., supra, Portera-Cailliau C. et al., supra, Lolley R. N. et al., Invest. *Ophthalmol Vis. Sci.* (1994), 35: 358–362.

Of great interest is the observation that photoreceptor degeneration occurs through apoptosis in response not only to genetic abnormalities, but also after experimental retina detachment. Cook, B E et al., *Invest. Ophthalmol. Vis. Sci.* (1995), 36: 990–996. Moreover, apoptotic cell death was also observed in acute retinal lesions in the albino rat induced by relatively low light levels and short exposure duration (1000 & 3000 lux, diffuse, white light for 2 hours), Réme et al., *Degenerative Diseases of the Retina*, Anderson R. E. et al, eds, Plenum Press, pp. 19–25 (1995). This discovery has lead to the search for survival-promoting trophic factors, factors which are believed to become unavailable to photoreceptors when the subretinal space expands and the composition of the interphotoreceptor matrix changes as a consequence of retinal detachment. Chader G. J. (1989), *Invest. Ophthalmol. Vis. Sci.* 30: 7–22; Berman E. R., *Biochemistry of the Eye* (1991), New York, N.Y., Plenum Press; Steinberg R. H., *Curr. Opin. Neurobiol.* 4: 515–24.

The death of photoreceptor cells through apoptosis is indicative that rather than being passive victims of the cumulative effects of mutations, photoreceptors die in genetic disorders such as retinitis pigmentosa by activation of their own "cell-death program." Adler, R. (1996) *Arch. Ophthalmol.* 114: 79–83. This implies that there is a role which certain neurotrophic factors and related molecules play in the degeneration of cones resulting from mutations in rod proteins.

The following examples are demonstrative of therapeutic utility because cell death occurs via apoptosis, the same mechanism as has been shown to occur in various retinal degenerative disorders. The knowledge that known growth factors prevented apoptosis correlated with preserved vision in animal models is indicative that prospective factors which prevent apoptosis would also have therapeutic utility in retinal degenerative disorders.

The following examples are offered by way of illustration and not by way of limitation. The disclosures of all citations in the specification are expressly incorporated herein by reference.

EXAMPLES

Example 1

Macular Holes

A patient pool with varying stages of macular holes (i.e., 2, 3 or 4) of varying ages are chosen and the presence of macular holes is confirmed. The pool is selected so as to exclude patients with histories of cystoid macula edema, diabetic retinopathy or exudative age-related macular degeneration.

Vision is examined in each subject to determine the best Snellen visual acuity and analyzed by intraocular pressure, fundus photographs, and fluorescein angiography. Each macular hole is graded according to the criteria described by Gass, *Arch. Ophthalmol.* (1988), 106: 629–39Eyes with Stage 2 holes have a retinal dehiscence along the margin of the areas of deep retinal cyst formation. Stage 3 is characterized by a full-thickness hole with overlying operculum. Macular holes are classified as Stage 4 when a posterior vitreous detachment is present. Treatment is scheduled within 2 weeks of the baseline examination. Under the criteria, patients should be excluded if they had greater than 2+ nuclear sclerotic or posterior subcapsular lens changes. Patients are followed for 6–10 months, with mean follow-up of 8 months. Doses are determined at a level below therapeutic effectiveness, in the middle of the effective range, and at a level well above the minimal effective range.

Eyes are randomly chosen for the indicated level of FGF-5. In addition, some eyes may separately receive 100 µl of intravitreal hyaluronic acid at the time of installation of FGF-5 in an attempt to delay clearance of FGF-5 from the area of the macular hole.

Surgical Procedure:

All surgery can be done under local anesthesia with sedation. After the eyes are prepped and draped, a standard three-port vitrectomy may be performed. In eyes with Stage 2 and Stage 3 macular holes, a core vitrectomy is performed. In Stage 4 macular hole, a complete pars plana vitrectomy is performed.

If encountered, an epiretinal membrane may be peeled from the surface of the retina and removed from the eye. In other cases, some gelatinous condensation on the inner surface of the retina surrounding the macular hole for about 200–400 µm, with a firm adhesion along the margin of the macular hole. This was carefully dissected where possible, taking care to limit traction on the edges of the macular hole and damage to the nerves.

After allowing for peripheral fluid to drain posteriorly, any fluid which migrates posteriorly is also aspirated. A tapered, bent-tipped cannula is then connected to a 1 cc syringe containing a solution of FGF-5. The reconstituted formulation contains the desired concentration of FGF-5 after dilution. Eyes are randomly assigned a dose of FGF-5. About 0.1 cc of FGF-5 solution is gently infused into the macular hole. The same volume of hyaluronic acid may also be administered.

After surgery, the patient should lie in a supine position for the first 24 hours following surgery. Thereafter, each patient should remain in a face-down position as much as possible for a 2 week period.

Patients are examined at 1 day, 2 weeks, 4–6 weeks, and monthly post surgery. Fluorescein angiography is performed at 4 to 6 weeks, 3 months, and 6 months. Best corrected Snellen visual acuity, intraocular pressure, lens status, bubble size, status of macular hole and occurrence of adverse effects are determined at each examination.

Discussion:

The rational for treatment in this example is to induce the flattening of the edges of the macular hole in order to resolve retinal detachment and thickening surrounding the hole. It has been suggested that a reduction in the traction force which elevates the retina around the hole coupled with and induction of the chorioretinal adhesion along the edge of the hole is necessary for therapeutic effect. Unlike peripheral retinal holes where surgical techniques can be used to reattach the retina and a small area of destruction is not noticeable, macular holes require gentle induction of chorioretinal adhesion to avoid the destruction of adjacent neurosensory tissue and permanent destruction of central vision.

Example 2

Light Induced Photoreceptor Injury

Albino rats (F344 of Sprague-Dawley) of 2–5 months of age are maintained in a cyclic light environment (12 hours on followed by 12 hours off from an in-cage illuminance of less than 25 ft-c) for 9 days or more days before exposure to a constant light source. The constant light source is maintained at an illuminance level of 115–200 ft-c. For example, 2 40 watt white reflector fluorescent bulbs suspended 60 cm above the floor of a transparent polycarbonate cage with stainless steel wire-bar covers.

Two days before the constant light exposure, the rats are anesthetized with a ketamine-xylazine mixture which is administered intravitreally with 1 µl of the tested factor dissolved in phosphate buffered saline (PBS) at a concentration of 50–1000 ng/µl. The injections were made with the insertion of a 32 gauge needle through the sclera, choroid and retina approximately midway between the ora serrata and equator of the eye. The factor-injected animals are compared to either uninjected littermates of those that receive control injections, as well as to control animals who are not exposed to constant light. Controls should include an injection of PBS alone, or a sham injection (insertion of needle with no injection). In all cases, the injections are made into the superior hemisphere of the eye.

Immediately following the constant light exposure, the rats are killed by any suitable means, e.g., carbon dioxide anesthetization followed by vascular perfusion of mixed aldehydes. The eyes are embedded in epoxy resin and sectioned into 1 µm thick sections of the entire retina along the vertical meridian of the eye. The degree of light-induced retinal degeneration is then quantified by two methods. The first is through measurement of the outer nuclear layer (ONL) thickness, which is used as an index of photoreceptor cell loss. A mean ONL thickness is obtained from a single section of each animal with the aid of a Bioquant morphometry system. In each of the superior and inferior hemispheres, ONL thickness is measured in 9 sets of 3 measurements each (total of 27 measurements in each hemisphere). Each set is centered on adjacent 440-µm lengths of retina (the diameter of the microscope field at 400× magnification). The first set of measurements is taken at approximately 440 µm from the optic nerve head, with subsequent sets taken more peripherally. Within each 440-µm length of the retina, the 3 measurements are made at defined points separated from one another by 75 µm. In all, 54 measurements are taken in the two hemispheres which sample representative regions of almost the entire retinal section.

The second method of assessing the degree of photoreceptor rescue is through a subjective evaluation by an examining pathologist on a scale of 0–4+, wherein 4+ is maximal rescue and nearly normal retinal integrity. The degree of photoreceptor rescue in each section, based in comparison to the control eye in the same rat, is scored by four individuals. This method not only takes into account the ONL thickness, but also more subtle degenerative changes to the photoreceptor inner and outer segments, as well as degenerative gradients within the eye.

Discussion:

The intravitreal administration of various factors into the eyes of albino rats can enable the rapid assessment of both the ability of the factors to rescue photoreceptors from degeneration and the side effects, such as incidence of macrophages, associated with each factor. Although the model described herein is the albino rat, the eyes of other albino mammals, such as mice and rabbits, are also useful for this purpose.

Example 3

Retinal Neuron Survival

Sprague Dawley rat pups at postnatal day 7 (mixed population: glia and retinal neuronal types) are killed by decapitation following $CO_2$ anesthesia and the eyes are removed under sterile conditions. The neural retina is dissected away from the pigment epithelium and other ocular tissue and then dissociated into a single cell suspension using 0.25% trypsin in $Ca^{2+}$, $Mg^{2+}$-free PBS. The retinas are incubated at 37 C for 7–10 m after which the trypsin is inactivated by adding 1 ml soybean trypsin inhibitor. The cells are plated at 100,000 cells per well in 96 well plates in DMEM/F12 supplemented with N2. Cells for all experiments are grown at 37 C in a water saturated atmosphere of 5% $CO_2$. After 2–3 days in culture, cells are stained with calcein AM then fixed using 4% paraformaldehyde and stained with DAPI for determination of total cell count. The total cells (fluorescent) are quantified at 20×objective magnification using CCD camera and NIH image software for MacIntosh. Fields in the well are chosen at random.

The effect of various concentration of FGF-5 (R&D Systems, cat. no. 237-F5/CF, lot no. GQ077040) (SEQ ID NO:5) are reported in FIG. 1.

Example 4

Rod Photoreceptor Survival

Sprague Dawley rat pups at 7 day postnatal (mixed population: glia and retinal neuronal cell types) are killed by decapitation following $CO_2$ anesthesis and the eyes are removed under sterile conditions. The neural retina is dissected away form the pigment epithelium and other ocular tissue and then dissociated into a single cell suspension using 0.25% trypsin in $Ca^{2+}$, $Mg^{2+}$-free PBS. The retinas are incubated at 37 C for 7–10 minutes after which the trypsin is inactivated by adding 1 ml soybean trypsin inhibitor. The cells are plated at 100,000 cells per well in 96 well plates in DMEM/F12 supplemented with N2Cells for all experiments are grown at 37° C. in a water saturated atmosphere of 5% $CO_2$. After 2–3 days in culture, cells are fixed using 4% paraformaldehyde, and then stained using CellTracker Green CMFDA. Rho 4D2 (ascites or IgG 1:100), a monoclonal antibody directed towards the visual pigment rhodopsin is used to detect rod photoreceptor cells by indirect immunofluorescence. The results are reported as % survival: total number of calcein—rhodopsin positive cells at 2–3 days in culture, divided by the total number of rhodopsin positive cells at time 2–3 days in culture. The total cells (fluorescent) are quantified at 20×objective magnification using a CCD camera and NIH image software for MacIntosh. Fields in the well are chosen at random.

The effect of various concentration of FGF-5 (R&D Systems, cat. no. 237-F5/CF, lot no. GQ077040) (SEQ ID NO:5) are reported in FIG. 1.

Example 5

Light Ablation Study

Introduction:

As indicated by Reme C. E. et al, *Degen. Dis. Retina*, Ch. 3, Ed. R. E. Anderson et al., Plenum Press, New York (1995), retina degeneration can be induced by exposure to strong light. This light ablation model permits a quantitative comparison of photoreceptor survival promoting activity of a tested substance.

Methods:

Adult female Sprague-Dawley rats were kept in "normal" fluorescent light environment (50 foot candles) for 12 hours on/off until the beginning of the experimental period. Light-induced degeneration was initiated by placing dark adapted (rats kept in 24 hour total darkness). About 5–10 animals in each treatment group were placed into a 5'×3' chamber illuminated with 490–580 nm (green) light at 300–400 foot candles. Light exposure was intermittent, 1 hour on, 2 hours off, for a total of eight cycles. Both eyes of each animal received 1–2 µl vitreal injections of test factor two days prior to the light exposure. Test factors employed were 0.5–1.0

µg/µl of bFGF (SEQ ID NO:4) or FGF-5 (R&D systems) (SEQ ID NO:5) and controls used were phosphate buffered saline with and without bovine serum albumin (0.1%).

Tdt-mediated dUTP nick-end labeling (TUNEL) (Gavrieli, Y et al., *J. Cell Biol.* 119: 493–501 (1992), was performed with modifications using the ApopTag® In Situ Apoptosis Detection Kit (Oncor, cat. no. S7110-KIT) on a 4 µm thick paraffin sections. The DNA strand breaks (fragments) were labeled with fluorescein while intact DNA were labeled with DAPI (4',6-diamidino-2-phenylindole) and visualized with a FITC/DAPI filter on a Vanox AH-3 Olympus microscope.

Figures 1, 9A:
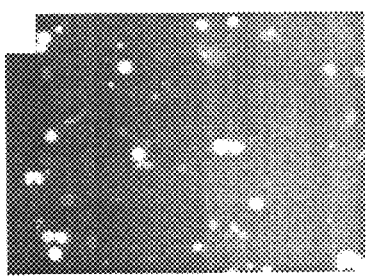
Figures 2, 9A:
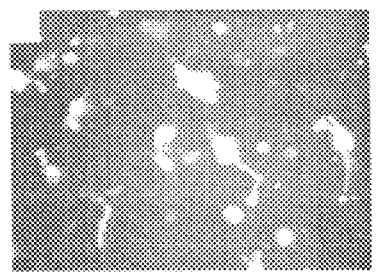
Figures 3, 9A:
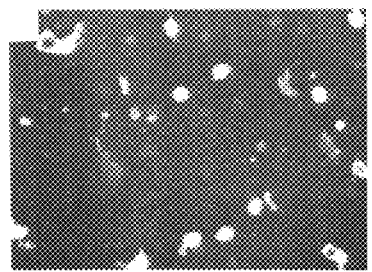
FIG. 3 is a positive image photograph of the retinal membranes of bFGF (SEQ ID NO:4), saline and FGF-5 (SEQ ID NO:5) treated samples graphically represented in FIG. 2.
Figures 1, 9B:
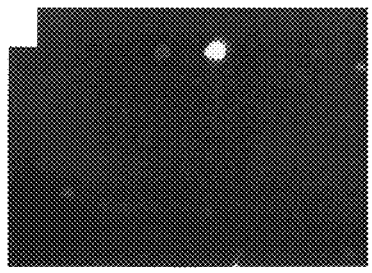
Figures 2, 9B:
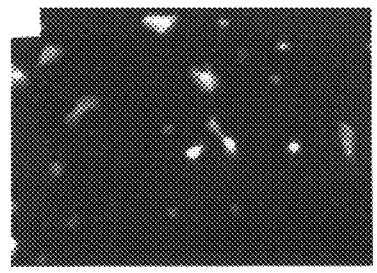
Figures 3, 9B:
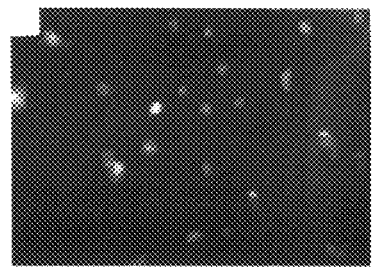
Figures 1, 9C:
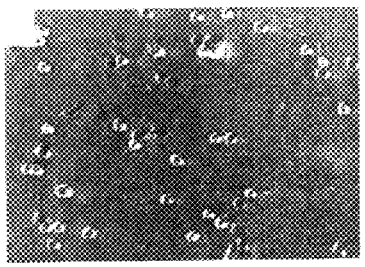
Figures 2, 9C:
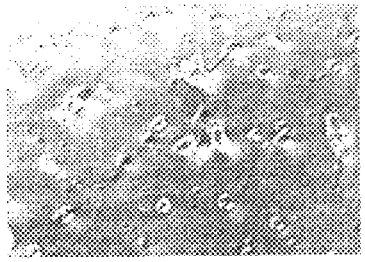
Figures 3, 9C:
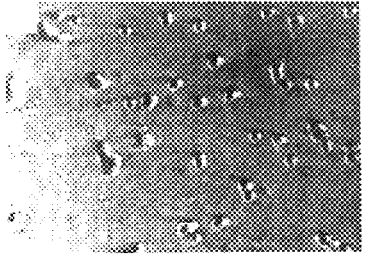

Results:

The degree of retinal degeneration or survival promoting activity of the tested factors is reported as the thickness of the photoreceptor cell layer or number of TUNEL labeled photoreceptor cell nuclei. Three transverse sections through the central retina (approx. 10 µm intervals) were used for the analysis. For each section, the entire retinal surface area was digitized using a cooled CCD camera and NIH image software (MacIntosh) to derive the quantitative data. The results are indicated graphically in FIG. 2. Pictographs of saline, bFGF (SEQ ID NO:4) and FGF-5 (SEQ ID NO:5) are indicated in FIG. 3. FIG. 4 is a pictograph of a control retina with no light exposure (a), at 50 hours post light cycling (b) and at 7 days post light cycling (c). FIG. 4 is representative of the normal degradation of photoreceptor cells which occurs upon exposure to intense light.

Figure 2:
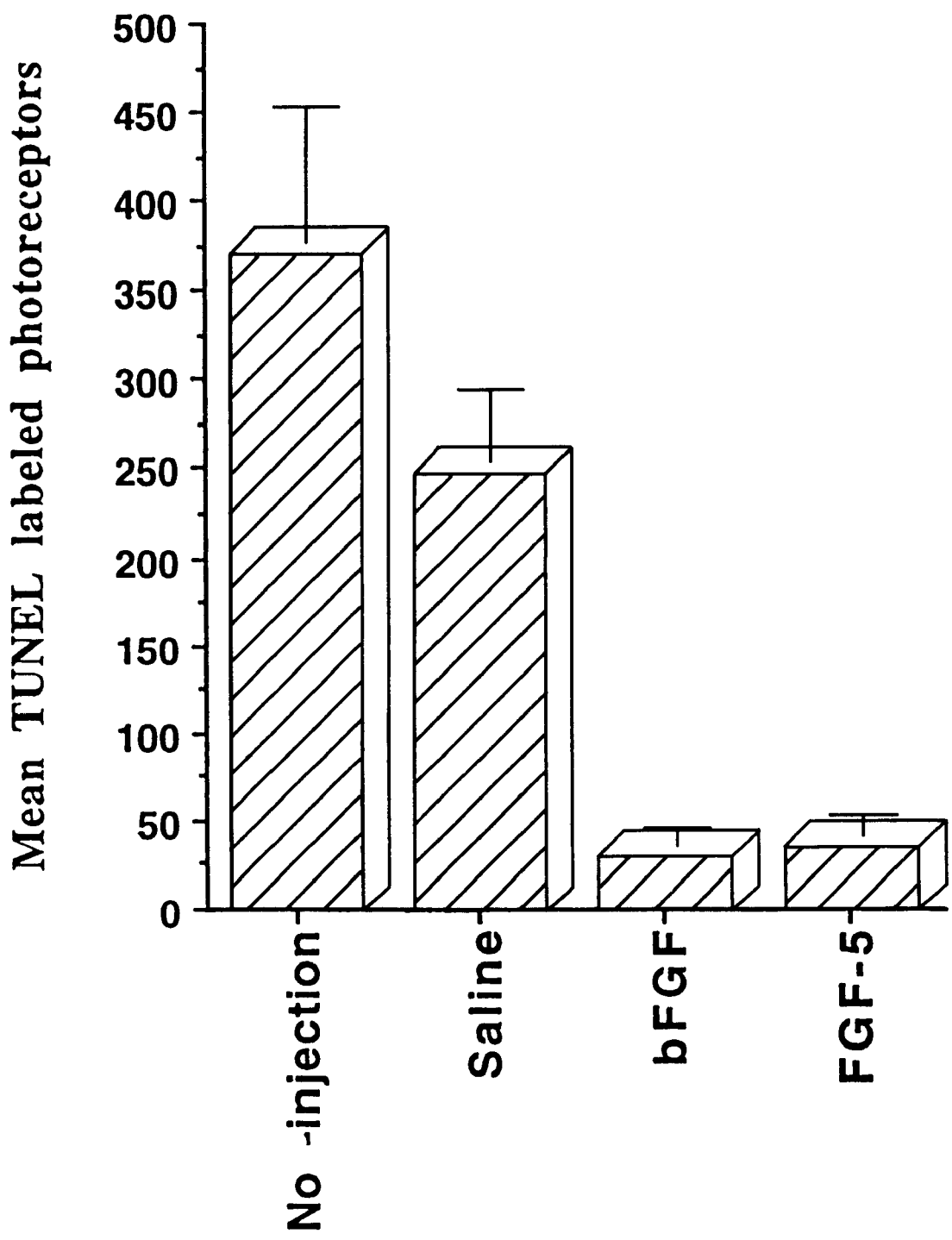
FIG. 2 is a bar graph of the TUNEL labeled photoreceptors in the presence of FGF-5 (SEQ ID NO:5), saline and bFGF (SEQ ID NO:4) in comparison with the control as administered by the procedure described in Example 5.

Conclusion:

FIG. 2 indicates that FGF-5 (SEQ ID NO:5) was at least as effective as bFGF and much more effective than the controls at preventing the death of photoreceptors as measured by TUNEL labeling. A comparison of FIGS. 3 with 4 further confirms this indication.

Example 6

Corneal Pocket Assay

Introduction:

This experiment is intended to determine whether the tested agent is angiogenic in this rodent in vivo model. Sample are formulated and pelleted with a delivery vehicle and stability and then transplanted into the cornea and then observed for angiogenic effect. The procedure has been adapted from Polverini et al., *Methods in Enzymology* 198: 440–450 (1991).

Methods:

Sprague-Dawley rats (250 g, male) were maintained in plastic carriers under darkened conditions 24 hours prior to treatment and then anesthetized. Each animal's eyes were gently proptosed and secured in place with nontraumatic forceps (BRI-1725). Using a No. 15 blade (Bard-Parker), a 1.5 mm incision was made approximately 1 mm from the center of the cornea into the stroma, but not through it. A curved spatula [2 mm wide, ASSIST 80017] was then inserted under the lip of the incision and gently blunt-dissected through the stroma toward the outer canthus of the eye. The final distance between the base of the pocket and the limbus should be at least 1 mm.

Pellets were prepared by mixing together tested growth factor (100 ng), sucralfate (50 µg, BM Research, Denmark) and Hydron (Interferon Sciences, New Brunswick, N.J., Lot #90005) in a 500:1 ratio of growth factor to sucralfate and Hydron (4 µl). The sucralfate is present to stabilize the molecule by interacting with the heparin-binding region. The control pellet was composed of Hydron and sucralfate vehicles only. Three treatment groups were tested composed of 1) bovine bFGF (SEQ ID NO:4) (Calbiochem, 10 µg/50 µl) PBS+sucralfate (6 animals); 2) sucralfate control (3 animals); and 3) FG-5 (R&D Systems, 50 ng, Lot #GQ127030) (SEQ ID NO:5)+sucralfate (6 animals).

A Hydron pellet (2×2 mm) prepared as described in the previous paragraph was inserted into the base of incision whereupon the pocket should reseal spontaneously. The eyes were coated with artificial tears ointment and then the animals were returned to their plastic carriers, then permitted to awaken and returned to their cages.

The assay was terminated on day 5. At time of sacrifice, the animals were perfused with FITC dextran ($2\times10^6$ m.w.) and corneal whole mounts prepared by careful dissection of the cornea from the eyes, followed by strategic placement of 2–3 cuts to permit permitting the cornea to lie flat, followed by placement under a coverslip. The image was captured through a 1×objective mounted on a Nikon inverted fluorescent scope. Image-Pro® software-edge detection routine was used to evaluate growth areas.

Figure 5:
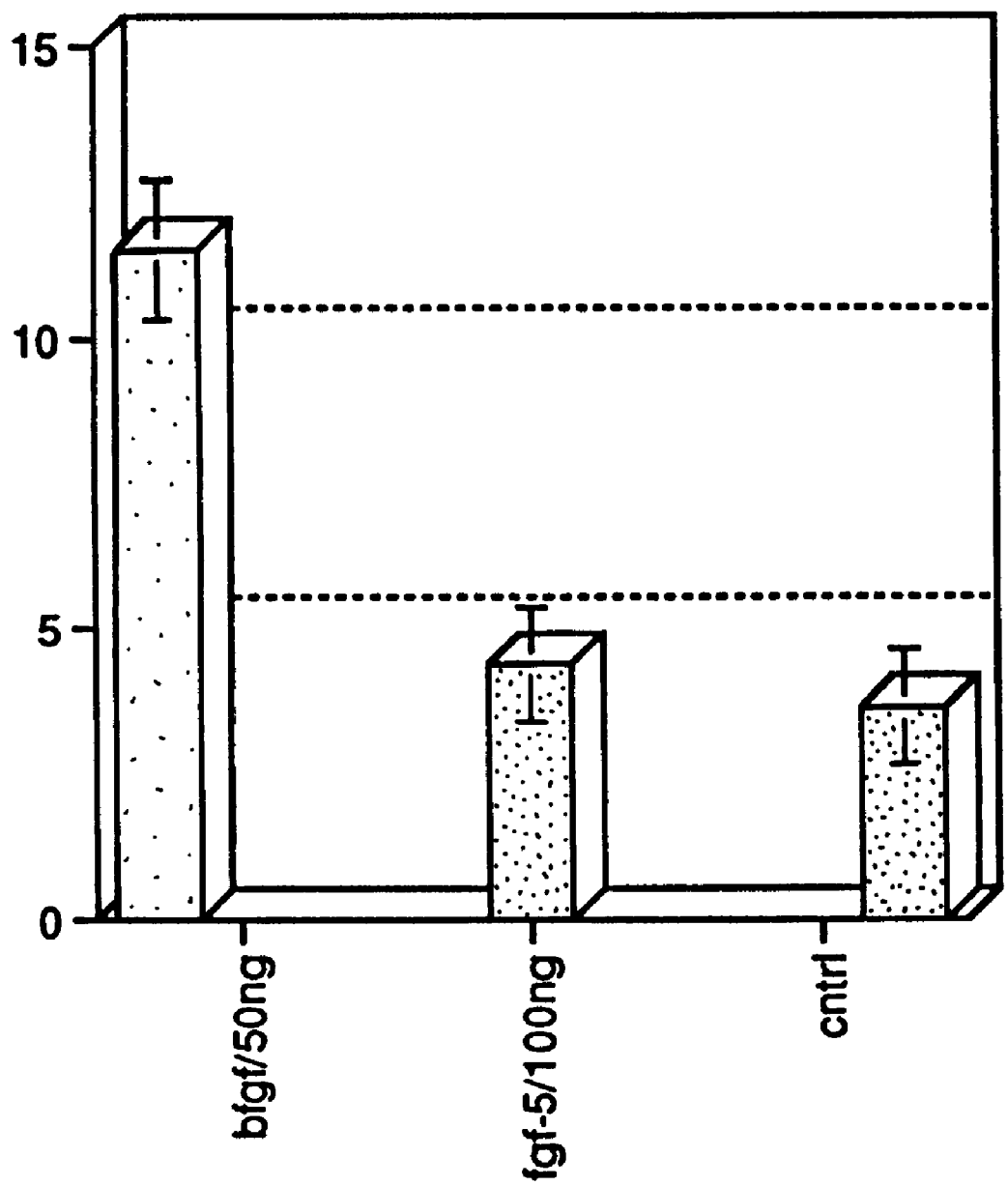
FIG. 5 is a bar graph representing the angiogenis observed after application of the indicated growth factors bFGF (SEQ ID NO:4) and FGF-5 (SEQ ID NO:5) according to the procedure described in Example 6.

Results and Conclusions:

In this experiment, the Sucralfate control group gave a mean value of 3.63±0.99 sq. mm. FgF-5 (SEQ ID NO:5) at 100 ng pellet gave a value of 4.37±0.99 sq. mm. which was not statistically different from the control (p=0.6204). bFGF (SEQ ID NO:4) at 50 ng/pellet gave a mean angiogenesis area of 11.54±1.18 which was significantly different from the control (p=0.0018) and FgF-5 (p=0.0010). These result are indicated in FIG. 5.

It is indicated by the data that even at a dosage of 100 ng/pellet that FGF-5 (SEQ ID NO:5) failed to demonstrate a significant angiogenic response.

Example 7

Vascular Endothelial Cell Mitogenecity Assay

Introduction:

Mitogenic assays on vascular endothelial cells were initially developed in order to monitor the purification of bFGF growth factor. However, they are also a useful measure to determine the presence of mitogenicity in the tested substance.

Materials and Methods:

Bovine adrenal cortex-derived capillary endothelial (ACE) cells are established according to known procedures as described by Ferrara et al., *Enzymology* 198, 391–405 (1991). Stock plates of ACE cells are were maintained in 10 cm tissue culture dishes in the presence of low glucose DMEM supplemented with 10% calf serum, 2 mM glutamine and penicillin G (1000 Units/mL) and streptomycin (1000 µg/mL) and basic FGF (SEQ ID NO:4) at a final concentration of 1 ng/ml and weekly passaged at a split ratio of 1:10. Mitogenic controls are prepared by adding basic FGF at final concentrations of 1 ng/ml and 5 ng/ml and culturing for 5–6 days. ACE cells can be passaged 10–12 times before showing signs of senescence.

For each the test substances, the stock cultures are trypsinized, resuspended in growth media, and seeded at a density of $1.0\times10^4$ cells/well in 6-well plates (Costar, Cambridge, Mass.), at a plating volume of 2 ml. FGF-5 samples to be tested are added to duplicate or triplicate wells in 10 µl aliquots, shortly after plating. After 5 or 6 days, cells are trypsinized and counted in a Coulter Counter (Coulter Electronics, Hialeah, Fla.).

Figure 6B:
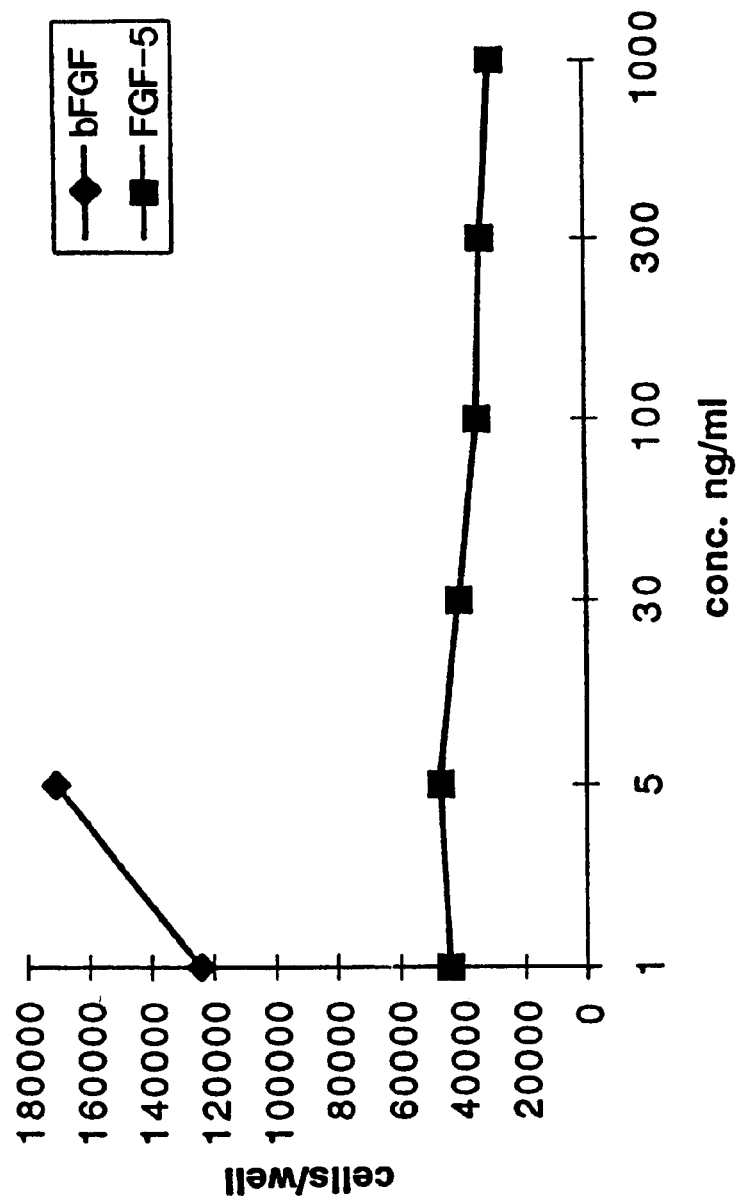
FIG. 6B is graph of concentration vs. cell count indicating the angiogenic effect of bFGF (SEQ ID NO:4) and FGF-5 (SEQ ID NO:5) at the indicated concentration. Note that bFGF was tested at 1 ng/ml and 5 ng/ml.

The results are also represented in FIGS. 6A and 6B. FIG. 6A represents the data depicted in Table 10, while FIG. 6B depicts a comparison of the observed effect between bFGF (SEQ ID NO:4) and FgF-5 (SEQ ID NO:5), wherein a concentration-dependent effect is apparent with bFGF (SEQ ID NO:4) and no concentration-dependent mitogenicity appears associated with FGF-5 (SEQ ID NO:5).

TABLE 10

ACE Bioassay

| Growth factor & (conc.) | Cell count 1 | Cell count 2 | Average ×20 |
| --- | --- | --- | --- |
| bFGF (SEQ ID NO:4) (1 ng/ml) | 6196 | 6234 | 124,300 |
| bFGF (SEQ ID NO:4) (5 ng/ml) | 8711 | 8377 | 170,880 |
| FGF-5 (SEQ ID NO:5) (1 ng/ml) | 2160 | 2279 | 44390 |
| FGF-5 (SEQ ID NO:5) (5 ng/ml) | 2491 | 2224 | 47150 |
| FGF-5 (SEQ ID NO:5) (30 ng/ml) | 2124 | 1981 | 41050 |
| FGF-5 (SEQ ID NO:5) (100 ng/ml) | 1629 | 1860 | 34890 |
| FGF-5 (SEQ ID NO:5) (300 ng/ml) | 1617 | 1746 | 33630 |
| FGF-5 (SEQ ID NO:5) (1 µg/ml) | 1585 | 1423 | 30080 |

Conclusion:

The data demonstrate that there is no concentration-dependent mitogenicity of FGF-5 (SEQ ID NO:5) at the concentrations 5 ng-1 µg.

What is claimed is:

1. A method of enhancing the survival of retinal cells in a mammal comprising administering a therapeutically effective amount of active FGF-5 polypeptide to said mammal.

2. The method of claim 1 wherein the active FGF-5 polypeptide is at least 90% homologous to a native sequence FGF-5 molecule.

3. The method of claim 1, where the active FGF-5 polypeptide is selected from the group consisting of SEQ ID NO: 2, SEQ ID NO: 3 and SEQ ID NO: 5.

4. The method of claim 1, wherein the retinal cells are selected from the group consisting of retinal neurons and supportive cells.

5. The method of claim 4 wherein the retinal neurons are selected from the group consisting of photoreceptors, retinal ganglion cells, displaced retinal ganglion cells, amacrine cells, displaced amacrine cells, horizontal and bipolar neurons.

6. The method of claim 4 wherein the supportive cells are selected from the group consisting of Müller cells and pigment epithelial cells.

7. The method of claim 4 wherein the retinal cells are photoreceptors.

8. The method of claim 1, wherein the administration method is intraocular.

9. The method of claim 1, wherein the polypeptide is administered into the vitreous or into the subretinal (interphotoreceptor) space.

10. The method of claim 1, wherein the administration method is intravitreal.

11. The method of claim 1, wherein the administration method is by means of an implant.

12. The method of claim 1, wherein the enhancement of survival of said retinal cells is associated with the treatment of an ocular disease, said ocular disease is selected from the group consisting of: retinitis pigmentosa; age related macular degeneration; retinal detachment; retinal tears; retinopathy; retinal degenerative diseases; macular holes; degenerative myopia; acute retinal necrosis syndrome; traumatic chorioretinopathies; contusion; edema; ischemic conditions; central retinal vision occlusion; branch retinal vision occlusion; collagen vascular diseases; thrombocytopenic purpura; uveitis; retinal vasculitis and occlusion.

13. An article of manufacture, comprising:

(a) a container;

(b) a label on said container; and (c) a composition contained within said container;

wherein the composition comprises an active FGF-5 effective for promoting the survival of retinal neurons, and the label on said container indicates that the composition can be used to enhance the survival of retinal neurons as a result of retinal disease.

14. The article of manufacture of claim 13 further comprising instructions for administering the FGF-5 polypeptide to a mammal.

15. The method of claim 3, wherein the active FGF-5 polypeptide is SEQ ID NO:2.

16. The method of claim 3, wherein the active FGF-5 polypeptide is SEQ ID NO:3.

17. The method of claim 3, wherein the active FGF-5 polypeptide is SEQ ID NO:5.

18. The method of claim 1 wherein the enhancement of survival of said retinal cells is associated with the treatment of an ocular disease, retinal injury, light or environmental trauma.

* * * * *

UNITED STATES PATENT AND TRADEMARK OFFICE
CERTIFICATE OF CORRECTION

PATENT NO. : 6,331,523 B1
DATED : December 18, 2001
INVENTOR(S) : Kljavin et al.

It is certified that error appears in the above-identified patent and that said Letters Patent is hereby corrected as shown below:

Column 1,
Line 29, delete "ones" and insert therefor -- cones --.
Line 42, delete "capillaris" and insert therefor -- capillaries --.

Column 5,
Line 24, delete " 754Intravitreal " and insert therefor -- 754. Intravitreal --.

Column 6,
Line 41, delete "3495The" and insert therefor -- 3495. The --.

Column 8,
Line 28, delete "angiogenis" and insert therefor -- angiogenesis --.

Column 14,
Line 24, delete "FGF-5Y anofsky" and insert therefor -- FGF-5. Yanofsky --.

Column 16,
Line 21, delete "FGF-5As" and insert therefor -- FGF-5. As --.
Line 57, delete "form"and insert therefor -- from --.

Column 17,
Line 2, delete "FGF-5Representative" and insert therefor -- FGF-5. Representative --.

Column 18,
Line 9, delete "cysteamnine" and insert therefor -- cysteamine --.

UNITED STATES PATENT AND TRADEMARK OFFICE
CERTIFICATE OF CORRECTION

PATENT NO. : 6,331,523 B1
DATED : December 18, 2001
INVENTOR(S) : Kljavin et al.

It is certified that error appears in the above-identified patent and that said Letters Patent is hereby corrected as shown below:

Column 20,
Line 11, delete "colagen" and insert therefor -- collagen --.

Signed and Sealed this

Thirtieth Day of April, 2002

Attest:

Attesting Officer

JAMES E. ROGAN
Director of the United States Patent and Trademark Office